US008101619B2

(12) United States Patent
Feenstra et al.

(10) Patent No.: US 8,101,619 B2
(45) Date of Patent: Jan. 24, 2012

(54) PHENYLPIPERAZINE DERIVATIVES WITH A COMBINATION OF PARTIAL DOPAMINE-$D_2$ RECEPTOR AGONISM AND SEROTONIN REUPTAKE INHIBITION

(75) Inventors: Roelof W. Feenstra, Weesp (NL); Axel Stoit, Weesp (NL); Jan-Willem Terpstra, Weesp (NL); Maria L. Pras-Raves, Weesp (NL); Andrew C. McCreary, Weep (NL); Bernard J. Van Vliet, Weep (NL); Mayke B. Hesselink, Weep (NL); Cornelis G. Kruse, Weep (NL); Gustaaf J. M. Van Scharrenburg, Weep (NL)

(73) Assignee: Solvay Pharmaceuticals B.V., Weesp (NL)

( * ) Notice: Subject to any disclaimer, the term of this patent is extended or adjusted under 35 U.S.C. 154(b) by 969 days.

(21) Appl. No.: 11/294,603

(22) Filed: Dec. 6, 2005

(65) Prior Publication Data

US 2006/0122190 A1   Jun. 8, 2006

Related U.S. Application Data

(60) Provisional application No. 60/634,074, filed on Dec. 8, 2004.

(51) Int. Cl.
A61K 31/496 (2006.01)
C07D 263/58 (2006.01)
(52) U.S. Cl. ................... 514/254.02; 544/368
(58) Field of Classification Search ............... 544/368; 514/254.02
See application file for complete search history.

(56) References Cited

U.S. PATENT DOCUMENTS 5,464,834 A   11/1995   Peglion et al.

FOREIGN PATENT DOCUMENTS

| DE | 487014 | 11/1929 |
|---|---|---|
| EP | 0 138 280 B1 | 4/1985 |
| EP | 0 189 612 B1 | 8/1986 |
| EP | 0 376 607 A1 | 7/1990 |
| EP | 0378 255 B1 | 7/1990 |
| EP | 0 900 792 | 3/1999 |
| GB | 1 378 080 | 12/1974 |
| WO | WO 97/36893 | 10/1997 |
| WO | WO 99/05140 | 2/1999 |
| WO | WO 99/51575 | 10/1999 |
| WO | WO 00/23441 | 4/2000 |
| WO | WO 00/43382 | 7/2000 |
| WO | WO 00/69424 A3 | 11/2000 |
| WO | WO 01/14330 A2 | 3/2001 |
| WO | WO 02/066473 A | 8/2002 |
| WO | WO 2004/020437 A1 | 3/2004 |
| WO | WO 2004/052886 A1 | 6/2004 |
| WO | WO 2004/054972 | 7/2004 |

OTHER PUBLICATIONS

Vippagunta et al. Advanced Drug Delivery Reviews, vol. 48, p. 3-26 (2001).*
Feenstra et al. Chemical Abstracts, vol. 130, No. 223299, Abstract for EP 900792 (Mar. 10, 1999) (1999).*
Wolff, Manfred E. Burger's Medicinal Chemistry, 5th Ed. Part 1, pp. 975-977 (1995).*
Robichaud et al. in Annualr Reports in Medicinal Chemistry, vol. 35, p. 11-20 (2000).*
TenBrink et al.. in Annual Reports in Medicinal Chemistry, vol. 29, p. 43-51 (1994).*
Banker et al. "Modern Pharmaceutics", 3rd Ed. p. 596 (1996).*
Creese, et al., "[$^3$H]-Spiroperidol Labels Dopamine Receptors in Pituitary and Brain," Eur. J. Pharmacol., vol. 46., pp. 377-381, (1977).
Habert, et al., "Characterisation of [$^3$H]-paroxetine Binding to Rat Cortical Membranes," Eur. J. Pharmacol., vol. 118, pp. 107-114, (1985).
Stella, "Prodrugs as Therapeutics," Expert Opin. Ther. Patents, vol. 14, No. 3, pp. 277-280, (2004).
King, "Bioisosteres, Conformational Restriction, and Pro-drugs— Case History: An Example of a Conformational Restriction Approach," Medicinal Chemistry: Principles and Practice, pp. 206-225, (ISBN 0-85186-494-5), (1994).
Organic Process Research and Development, vol. 1, No. 4, pp. 300-310, (1997).
Ettmayer, et al., "Lessons Learned from Marketed and Investigational Prodrugs," J. Med. Chem., 47, pp. 2393-2404, (2004).
Van Der Heyden, et al., "A Rapidly Acquired One-Way Conditioned Avoidance Procedure in Rats as a Primary Screening Test for Antipsychotics: Influence of Shock Intensity on Avoidance Performance", Behavioural Brain Research, vol. 31, pp. 61-67, (1998).

(Continued)

*Primary Examiner* — Emily Bernhardt
(74) *Attorney, Agent, or Firm* — Finnegan, Henderson, Farabow, Garrett & Dunner, L.L.P.

(57) ABSTRACT

The invention relates to a group of novel phenylpiperazine derivatives with a dual mode of action: serotonin reuptake inhibition and partial agonism on dopamine-$D_2$ receptors. The invention also relates to the use of a compound disclosed herein for the manufacture of a medicament giving a beneficial effect.
The compounds have the general formula (1):

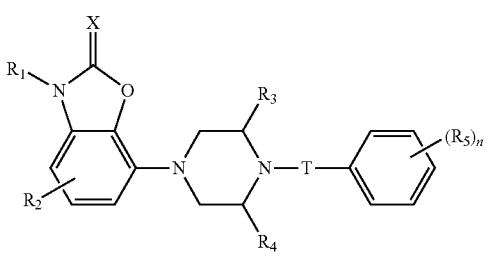

(1)

wherein the symbols have the meanings given in the specification,
and tautomers, stereoisomers and N-oxides thereof, as well as pharmacologically acceptable salts, hydrates and solvates of said compounds of formula (1) and its tautomers, stereoisomers and N-oxides.

8 Claims, No Drawings

OTHER PUBLICATIONS

Van Der Poel, et al., "Temporal Patterning of Ultrasonic Distress Calls in the Adult Rat: Effects of Morphine and Benzodiazepines", Psycho-pharmacology, vol. 97, pp. 147-148, (1989).
International Preliminary Report on Patentability, dated Apr. 10, 2007, International Application No. PCT/EP2005/056507.
Adcock, et al., "Fluorine-19 Substituent Chemical Shifts," Aust. J. Chem. vol. 23, pp. 1921-1937, (1970).
Badger, et al., "Thionaphthencarboxylic Acids," Journal of the Chemical Society, pp. 2624-2630, (1957).
Beattie, et al., "The Synthesis of Nine Chloroidonaphthalenes," Journal of the Chemical Society, pp. 50-52, (1934).
Berg, et al., "The Search for Chemotherapeutic Amidines. Part X Substituted 4:4'-Diamidino-aw-diphenoxyalkanes and -diphenyl Ethers," Journal of the Chemical Society, pp. 642-648, (1949).
Bickel, "The Pharmacology and Biochemistry of N-Oxides," Pharmacological Reviews, 21(4), pp. 325-355, (1969).
Boschman, et al., "Invitro inhibition of ADP-induced platelet Aggregation by O-(aminoalkyl) oxime ethers," European J. of Medicinal Chem., vol. 15, No. 4, pp. 351-356 (Jul. 1980).
Buchan, et. al., "The Chlorination of Iodophenols. The Chlorination of o-Iodophenol," Journal of the Chemical Society, pp. 137-145, (1931).
Campos et al., "A General Synthesis of Substituted Indoles from Cyclic Enol Ethers and Enol Lactones," Organic Letters, vol. 6, No. 1, pp. 79-82, (2004).
Costall et al., "Climbing Behavior Induced by Apormorphine in Mice: A Potential Model for the Detection of Neurolaptic Activity," Eur. J. Pharmacol., vol. 1, pp. 39-50 (1978).
Davison et al., "Nitrone dipolar Cycloaddition routes to piperidines and indolizidines, Part 9. Formal synthesis of (−)-pinidine and total synthesis of (−)-histrionicotoxin, (+)-histrionicotoxin and (−)-histrioncotoxin 235A," J. Chem. Soc., Perkins Trans. 1, pp. 1494-1514, (2002).
Feenstra et al. "Antiparkinsonian Antidepressant Anxiolytic Dopamine D2 Partial Agonist 5-HT 1a Agonist," Drugs of the Future, vol. 26, No. 2, pp. 128-132, (2001).
Feenstra et al., "New 1-aryl-4-(biarylmethylene)piperazines as potential atypical antipsychotics sharing dopamine D2 receptor and serotonin 5HT1A receptor affinities," Bioorg. & Med. Chem. Lett., 11, pp. 2345-2349 (2001).
Finger et al., "Aromatic Fluorine Compounds," Plant Growth Regulators and Intermediates, pp. 94-101, 1959.
Huang et al., "Expanding Pd-Catalyzed C-N Bond-Forming Processes: The First Amidation of Aryl Sulfonates, Aqueous Amination, and Complementarity with Cu-Catalyzed Reactions," J. Am. Chem. Soc., vol. 125, No. 22, pp. 6653-6655, (2003).
Jacobs, B.L., "An Animal Behaviour Model for Studying Central Seratongergic Synapses," Life Sci., vol. 19, No. 6, pp. 777-785 (1976).
Leclerc, et al., "5-Halobenzothiophene Analogues of Melatonin: Synthesis and Affinity for mt1 and MT2 Receptors in Man," Pharm. Pharmacol. Commun., pp. 61-65, (2000).
Mancuso, et al., "Activated Dimethyl Sulfoxide: Useful Reagents for Synthesis, Int'l. Journal of Methods in Synthetic Organic Chemistry," pp. 165-185, (1981).
Ruchardt et al., "Durchfuhrung der Jacobsonschen Indazolsynthese im Eintopfverfahren," Liebigs Ann. Chem, pp. 908-927, (1980).
Weiss et al., "Corticotropin-Peptide Regulation of Intracellular Cyclic AMP Production in Cortical Neurons in Primary Culture," Journal of Neurochemistry, vol. 45, No. 3, pp. 869-874, (1985).
Searles, "The Reaction of Trimethylene Oxide with Grignard Reagents and Organolithium Compounds," vol. 73, p. 124-125, (1951).
Timms, et al. "SAR Development of a Selective 5-HT1D Antagonist/Serotonin Reuptake Inhibitor Lead Using Rapid Parallel Synthesis," Bioorg. Med. Chem. vol. 14, No. 10, pp. 2469-2472, (2004).
Van Hes, et al., "SLV310, A Novel, Potential Antipsychotic, Combining Potent Dopamine D2 Receptor Antagonism with Serotonin Reuptake Inhibition," Biorg. Med. Chem., vol. 13, No. 3, pp. 405-408, (2003).
Yoram Solomon, et al., "A Highly Sensitive Adenylate Cyclase Assay," Analytical Biochemistry 58, pp. 541-548, (1974).
Yu, et al., "20-Hydroxyeicosatetraenoic Acid (20-HETE): Structural Determinants for Renal Vasoconstriction," Bioorg. Med. Chem. 11, pp. 2803-2821, (2003).

* cited by examiner

PHENYLPIPERAZINE DERIVATIVES WITH A COMBINATION OF PARTIAL DOPAMINE-$D_2$ RECEPTOR AGONISM AND SEROTONIN REUPTAKE INHIBITION

CROSS REFERENCE TO RELATED APPLICATION

This application claims the benefit of U.S. Provisional Application No. 60/634,074, filed Dec. 8, 2004, the content of which is incorporated herein by reference.

The present invention relates to a group of novel and phenylpiperazine derivatives with a dual mode of action: serotonin reuptake inhibition and partial agonism on dopamine-$D_2$ receptors. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of disorders in which dopamine-$D_2$ receptors and serotonin reuptake sites are involved, or that can be treated via manipulation of those targets.

Compounds with a dual action as dopamine-$D_2$ antagonists and serotonin reuptake inhibitors are known from WO 00/023441, WO 00/069424 and WO 01/014330. This combination of activities is useful for the treatment of schizophrenia and other psychotic disorders: it enables a more complete treatment of all disease symptoms. Benzoxazolone derivatives bearing a terminal phenyl group are disclosed in EP 0 900 792 A1. Those compounds however, have a dual action as dopamine-$D_2$ antagonists and 5-$HT_{1A}$ agonists, and are devoid of serotonin reuptake inhibition.

The goal of the present invention was to provide further compounds with a dual action as partial dopamine-$D_2$ antagonists and serotonin reuptake inhibitors.

The invention relates to a group of novel compounds of the formula (1):

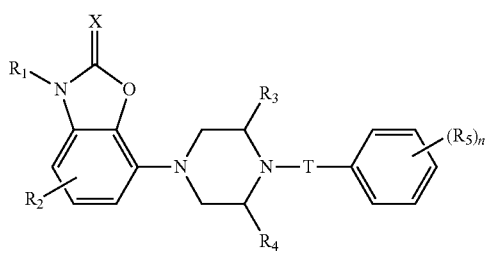

(1)

wherein:
X=S or O,
$R_1$ is H, $(C_1-C_6)$alkyl, $CF_3$, $CH_2CF_3$, OH or O—$(C_1-C_6)$alkyl
$R_2$ is H, $(C_1-C_6)$alkyl, halogen or cyano
$R_3$ is H or $(C_1-C_6)$alkyl
$R_4$ is H, $(C_1-C_6)$alkyl, optionally substituted with a halogen atom,
T is a saturated or unsaturated carbon chain of 2-7 atoms, wherein one carbon atom may be replaced with a nitrogen atom, optionally substituted with an $(C_1-C_3)$-alkyl, $CF_3$ or $CH_2CF_3$ group, an oxygen atom or a sulphur atom, which chain is optionally substituted with one or more substituents selected from the group consisting of $(C_1-C_3)$alkyl, $(C_1-C_3)$alkoxy, halogen, cyano, trifluoromethyl, $OCF_3$, $SCF_3$, $OCHF_2$ and nitro,
$R_5$ is a substituent selected from the group consisting of $(C_1-C_3)$alkyl, $(C_1-C_3)$alkoxy, halogen, cyano, trifluoromethyl, $OCF_3$, $SCF_3$, $OCHF_2$ and nitro,
n has the value 0-5,
and tautomers, stereoisomers and N-oxides thereof, as well as pharmacologically acceptable salts, hydrates and solvates of said compounds of formula (1) and its tautomers, stereoisomers and N-oxides,
with the proviso that when, X=O, $R_1$ is hydrogen or methyl, $R_2$ is hydrogen and n=1, $R_5$ is not 4-fluoro.

In the description of the substituents the abbreviation 'alkyl $(C_{1-3})$' means 'methyl, ethyl, n-propyl or isopropyl'.

Prodrugs of the compounds mentioned above are in the scope of the present invention. Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, Ed.: F. D. King, p. 215; J. Stella, "Prodrugs as therapeutics", Expert Opin. Ther. Patents, 14(3), 277-280, 2004; P. Ettmayer et al., "Lessons learned from marketed and investigational prodrugs", J. Med. Chem., 47, 2393-2404, 2004). Pro-drugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine; a Mannich base, a hydroxyl-methylene derivative, an O-(acyloxy-methylene carbamate) derivative, carbamate, ester, amide or enaminone.

N-oxides of the compounds mentioned above are in the scope of the present invention. Tertiary amines may or may not give rise to N-oxide metabolites. The extend to what N-oxidation takes place varies from trace amounts to a near quantitative conversion. N-oxides may be more active than their corresponding tertiary amines or less active. Whilst N-oxides are easily reduced to their corresponding tertiary amines by chemical means, in the human body this happens to varying degrees. Some N-oxides undergo nearly quantitative reductive conversion to the corresponding tertiary amines, in other cases the conversion is a mere trace reaction or even completely absent. (M. H. Bickel: "The pharmacology and Biochemistry of N-oxides", Pharmaco-logical Reviews, 21(4), 325-355, 1969).

It has been found that the compounds according to the invention show high affinity for both the dopamine $D_2$ receptor and the serotonin reuptake site. The compounds show activity at dopamine $D_2$ receptors with varying degree of agonism. All of the compounds show activity as inhibitors of serotonin reuptake, as they potentiate 5-HTP induced behaviour in mice (B. L. Jacobs., 'An animal behaviour model for studying central serotonergic synapses', Life Sci., 1976, 19(6), 777-785).

In contrast to the use of full dopamine-$D_2$ receptor agonists or antagonists, the use of partial dopamine-$D_2$ receptor agonists offers a dynamic medication that self-adjusts on a moment-to-moment basis to the endogenous state of the patient. Thus, it provides the desired flexible modulation of the dopamine system and avoidance of the many adverse effects caused either by treatment using full dopamine-$D_2$ receptor agonists like bromocriptine (hallucinations, nausea, vomiting, dyskinesia, orthostatic hypotension, somnolescence) or full dopamine-$D_2$ receptor antagonists like haloperidol (emotional blunting, dysphoria, tardive dyskinesia). Because of these many adverse effects, full agonists and antagonists have found only very limited use in the therapy of depressive and anxiety disorders. Partial dopamine-$D_2$ receptor agonists not only show a flexible modulation and a favourable side-effect profile, they also have a pronounced anxiolytic profile in relevant animal models (Drugs of the Future 2001, 26(2): 128-132).

Partial dopamine-$D_2$ receptor agonists, according to the present invention, are compounds that—when tested in a concentration response range—achieve activation in the functional cAMP cell based assay (as described below). Partial dopamine-$D_2$ receptor agonists will act as an agonist in cases when the endogenous synaptic tone of dopamine is low, or in the presence of a full dopamine-$D_2$ receptor antagonist, and will act as an antagonist in cases when the endogenous synaptic tone of dopamine is high, or in the presence of a full dopamine $D_2$ receptor agonist. Like full agonists, partial dopamine-$D_2$ receptor agonists in general are active in sensitized systems. They induce contralateral turning in rats with unilateral 6-hydroxy-dopamine (6-OHDA) lesions in the substantia nigra pars compacta. In MPTP-treated common marmosets they produce potent and long-lasting reversal of motor symptoms (Drugs of the Future 2001, 26(2): 128-132). In contrast to full agonists, however, partial dopamine-$D_2$ agonists are substantially less active in non-sensitized systems: they hardly reverse reserpine induced hypolocomotion in rats.

For the treatment of CNS disorders involving an overactive dopaminergic system a pharmaceutical preparation combining partial dopamine-$D_2$ receptor agonistic activity having low intrinsic functional activity with serotonin reuptake inhibitory activity is recommended. In case of a disorder involving dopamine insufficiency a pharmaceutical preparation combining partial dopamine-$D_2$ receptor agonistic activity with high intrinsic functional activity and serotonin reuptake activity according to the invention has considerable advantages.

Disorders characterized by dynamic fluctuations in dopamine neurotransmission like bipolar depression and addiction will profit in particular from the flexible adjustment of the dopamine system by the partial dopamine-$D_2$ receptor agonists in the pharmaceutical preparation. Combining this "dopaminergic neurotransmission stabilizing" activity with serotonin reuptake inhibitory activity will enhance antidepressive and anxiolytic efficacy. The compounds can be used for the treatment of affections or diseases of the central nervous system caused by disturbances in the dopaminergic and serotonergic systems, for example: aggression, anxiety disorders, autism, vertigo, depression, disturbances of cognition or memory, Parkinson's disease, and in particular schizophrenia and other psychotic disorders.

Pharmaceutically acceptable salts may be obtained using standard procedures well known in the art, for example by mixing a compound of the present invention with a suitable acid, for instance an inorganic acid such as hydrochloric acid, or with an organic acid.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

In Vitro Affinity for Dopamine-$D_2$ Receptors

Affinity of the compounds for dopamine-$D_2$ receptors was determined using the receptor binding assay described by 1. Creese, R. Schneider and S. H. Snyder: "[$^3$H]-Spiroperidol labels dopamine receptors in rat pituitary and brain", Eur. J. Pharmacol., 46, 377-381, 1977.

In Vitro Affinity for Serotonin Reuptake Sites

Affinity of the compounds for serotonin reuptake sites was determined using the receptor binding assay described by E. Habert et al.: "Characterisation of [$^3$H]-paroxetine binding to rat cortical membranes", Eur. J. Pharmacol., 118, 107-114, 1985.

Inhibition of Forskolin-Induced [$^3$H]-cAMP Accumulation

The in vitro functional activity at dopamine-$D_2$ receptors, including the intrinsic activity ($\epsilon$) of the compounds of the invention was measured by their ability to inhibit forskolin-induced [$^3$H]-cAMP accumulation.

Human dopamine $D_{2,L}$ receptors were cloned in fibroblast cell line CHO-K1 cells and obtained from Dr. Grandy, Vollum Institute, Portland, Oreg., USA. CHO cells were grown in a Dulbecco's modified Eagle's medium (DMEM) culture medium, supplemented with 10% heat-inactivated fetal calf serum, 2 mM glutamine, 1 mM pyruvate, 5000 units/ml penicillin, 5000 μg/ml streptomycin and 200 μg/ml G-418 at 37° C. in 93% air/7% $CO_2$. For incubation with test compounds, confluent cultures grown in 24 wells plates were used. Each condition or substance was routinely tested in quadruplicate. Cells were loaded with 1 μCi [$^3$H]-adenine in 0.5 ml medium/well. After 2 hours, cultures were washed with 0.5 ml PBS containing 1 mM of the phosphodiesterase inhibitor isobutylmethylxanthine (IBMX) and incubated for 20 min with 0.5 ml PBS containing 1 mM IBMX and forskolin with or without test compound. After aspiration the reaction was stopped with 1 ml trichloroacetic acid 5% (w/v). The [$^3$H]-ATP and [$^3$H]-cAMP formed in the cellular extract were assayed as described by Solomon Y, Landos C, Rodbell M, 1974, A highly selective adenylyl cyclase assay, Anal Biochem 58:541-548 and Weiss S, Sebben M, Bockaert J J, 1985, Corticotropin-peptide regulation of intracellular cyclic AMP production in cortical neurons in primary culture, J Neurochem 45:869-874. 0.8 ml Extract was passed over Dowex (50WX-4 200-400 mesh) and aluminumoxide columns, eluted with water and 0.1M imidazole (pH=7.5). Eluates were mixed with 7 ml Insta-gel and radioactivity was counted with a liquid scintillation counter. The conversion of [$^3$H]-ATP into [$^3$H]-cAMP was expressed as the ratio in percentage radioactivity in the cAMP fraction as compared to combined radioactivity in both cAMP and ATP fractions, and basal activity was subtracted to correct for spontaneous activity.

Test compounds were obtained as 10 mM stock solutions in 100% DMSO, and diluted in PBS/IBMX to final concentrations. Typically, compounds were used in concentrations that ranged from $10^{-10}$M to $10^{-5}$M. From quadruplicate data counts, the mean was taken as an estimate for drug-induced, receptor-mediated effects at specified second messenger accumulation, expressed as percentage of control values (forskolin-stimulated cAMP accumulation, subtracted by basal activity). By using the non-linear curve-fitting program INPLOT or the Excel-add-in XL-Fit, mean values were plotted against drug concentration (in molar) and a sigmoid curve (four-parameter logistic curve) was constructed. The maximal forskolin-induced stimulated conversion is taken as maximum value and the maximal inhibition (usually at drug concentrations $10^{-6}$ M or $10^{-5}$ M) as minimum and these values were fixed during the fitting process. Thus, concentrations of the compound, causing 50% of the maximally obtained inhibition of forskolin-induced cAMP accumulation ($EC_{50}$), are averaged over several experiments and presented as mean $pEC_{50} \pm SEM$. Antagonist potency is assessed by co-incubating cells with a fixed agonist concentration and specified antagonist concentrations. Curve fitting procedures are identical to those used for estimating $EC_{50}$ values. Thus $IC_{50}$ values, i.e. the concentration that is able to achieve 50% of maximal antagonism that can be achieved by this compound. $IC_{50}$ values are corrected using a Cheng-Prussoff equation, correcting it for agonist concentration and $EC_{50}$ values that is obtained in the same experiment. Thus, $K_b=IC_{50}/(1+[\text{agonist}]/EC_{50}, \text{agonist})$. The corresponding $pA_2$ value is $-\log(K_b)$. Concentration-response curve fitting allows estimation of $pEC_{50}$ values and of maximal achievable effect (intrinsic activity or efficacy ($\epsilon$). A full receptor agonist has $\epsilon=1$, a full receptor antagonist has $\epsilon=0$, and a partial receptor agonist has an intermediate intrinsic activity.

Dosages

The affinity of the compounds of the invention for dopamine-$D_2$ receptors and serotonine reuptake sites was determined as described above. From the binding affinity measured for a given compound of formula (1), one can estimate a theoretical lowest effective dose. At a concentration of the compound equal to twice the measured $K_i$-value, 100% of the receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, preferably 0.1-100 mg/kg of patient's bodyweight.

Treatment

The term 'treatment' as used herein refers to any treatment of a mammalian, preferably human condition or disease, and includes: (1) inhibiting the disease or condition, i.e., arresting its development, (2) relieving the disease or condition, i.e., causing regression of the condition, or (3) relieving the conditions caused by the disease, i.e., stopping the symptoms of the disease.

The preparation of the compounds having formula (I) will now be described in more detail in the following Examples.

EXAMPLES

The H-atom of the N—H moiety of the phenylpiperazine part of the compounds of formula (1), the 'amines' I-H to IX-H can be replaced by Q by the general method A (see above) leading to the compounds of the invention which are listed in table 1 (see below).

Method A:

The compounds were prepared via the synthesis depicted in scheme A1: an amine was reacted with Q-X (X=leaving group like e.g. Cl, Br, I) in e.g. acetonitrile or butyronitrile with Et(i-Pr)$_2$N acting as a base, in some cases KI (or NaI) was added. Et$_3$N can be used instead of Et(i-Pr)$_2$N.

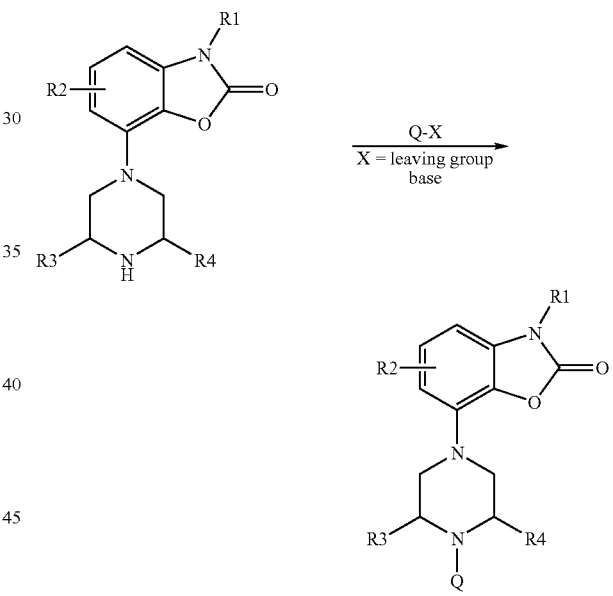

Example 1

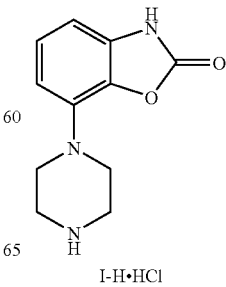

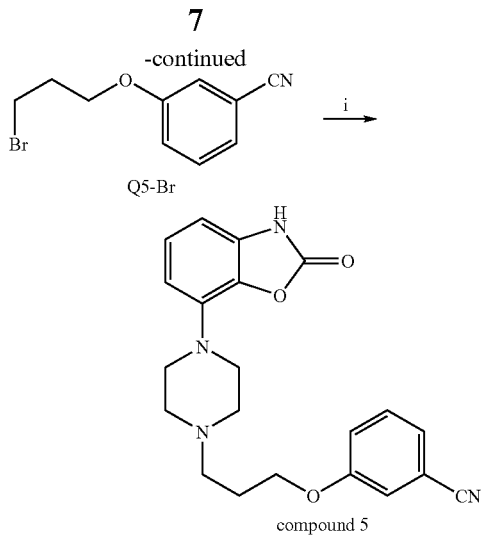

compound 5

Scheme A2, Step i:

A suspension of the piperazine hydrochloride I-H.HCl (5.11 g, 20 mmol), 6.0 g (25 mmol) of the bromide, KI (7.75 g) and DIPEA (10.6 ml; 60 mmol) in 75 ml acetonitril was heated on an oilbath at reflux under nitrogen for 20 hours. After cooling down to room temperature the suspension was filtered with suction and concentrated in vacuo. Purification by column chromatography on silica gel (eluent: DCM/MeOH/NH$_3$=920/75/5) gave two fractions of compound 5 (both 2.9 g) which were together recrystallised from 75 ml of acetonitril, yielding 4.48 g of compound 5 as an off-white solid. M.p.: 145-9° C.

TABLE 1 examples of compounds of the invention.

| comp | amine | Group Q | meth. | L-group | salt | melting r. ° C. |
|---|---|---|---|---|---|---|
| 1 | I | 1 | A | Br | free base | 169-171 |
| 2 | I | 2 | A | Br | free base | 150-152 |
| 3 | I | 3 | A | Br | HCl | 238-240 |
| 4 | I | 4 | A | Br | free base | 139-142 |
| 5 | I | 5 | A | Br | free base | 145-149 |
| 6 | I | 6 | A | Br | free base | 165-168 |
| 7 | I | 7 | A | Br | FUM | 170-175 |
| 8 | I | 8 | A | Br | free base | 166-169 |
| 9 | I | 9 | A | Br | free base | 153-155 |
| 10 | I | 10 | A | Br | free base | 180-183 |
| 11 | I | 11 | A | Br | free base | 130-132 |
| 12 | I | 12 | A | I | free base | 178-179 |
| 13 | I | 13 | A | I | free base | 170-171 |
| 14 | I | 15 | A | I | HCl | 230-231 |
| 15 | I | 16 | A | I | HCl | 195-196 |
| 16 | I | 17 | A | I | HCl | 229-231 |
| 17 | I | 18 | A | Br | free base | 140-142 |
| 18 | I | 19 | A | Br | free base | 84-86 |
| 19 | I | 20 | A | I | free base | 166-168 |
| 20 | I | 21 | A | I | HCl | 168-170 |
| 21 | I | 22 | A | I | free base | 146-148 |
| 22 | I | 23 | A | I | HCl | 161-163 |
| 23 | I | 24 | A | Br | free base | 164-166 |
| 24 | I | 25 | A | Br | free base | 189-190 |
| 25 | I | 26 | A | Br | free base | 151-153 |
| 26 | II | 5 | A | Br | HCl | 251-254 |
| 27 | II | 6 | A | Br | HCl | 230-235 |
| 28 | II | 17 | A* | I | free base | 156-8 |
| 29 | V | 5 | A | Br | free base | 147-149 |
| 30 | V | 6 | A | Br | free base | 123-125 |
| 31 | V | 9 | A | Br | free base | 95-97 |
| 32 | V | 13 | A | I | free base | 152-154 |
| 33 | V | 14 | A | I | HCl | 174-176 |
| 34 | V | 16 | A | I | HCl | 216-218 |
| 35 | V | 17 | A* | I | free base | 87-9 |

TABLE 1-continued examples of compounds of the invention.

| comp | amine | Group Q | meth. | L-group | salt | melting r. ° C. |
|---|---|---|---|---|---|---|
| 36 | VI | 5 | A | Br | free base | 171-2 |
| 37 | VI | 6 | A | Br | HCl | 242-4.5 |

*see scheme 12-17b

Structures of the phenylpiperazine part of the compounds of formula (1), herein termed 'amines', and groups 'Q' are given below. In the column 'method', the general method is given and the next column gives the leaving group.

The piperazines used in these methods are indicated as I-H to IX-H:

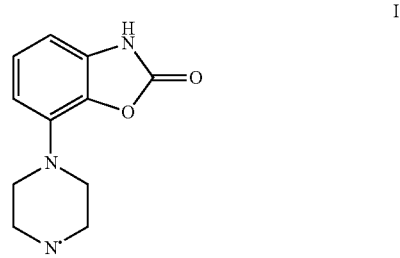

I

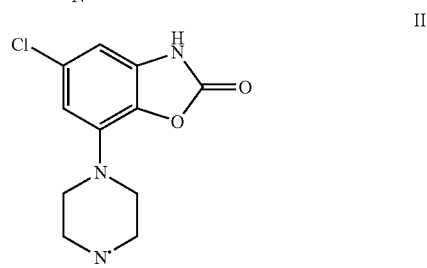

II

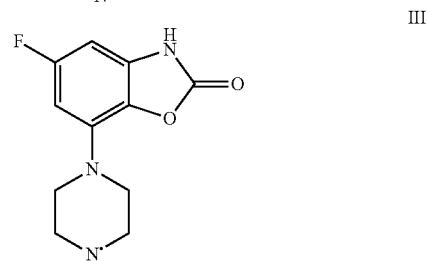

III

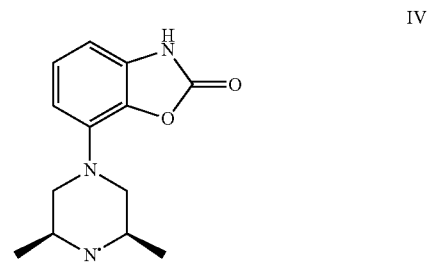

IV

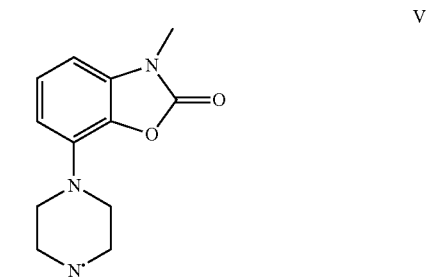

V

VI 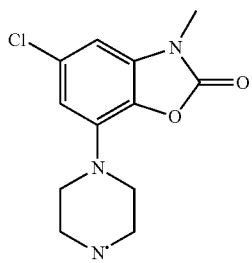

VII 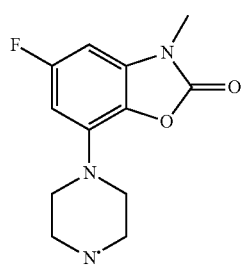

VIII 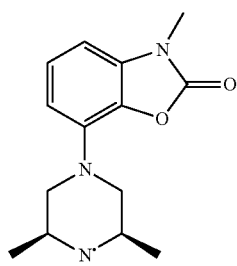

IX 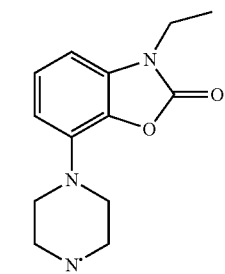

The syntheses of the piperazines I-H, III-H and V-H are described in WO97/36893.

Synthesis of Amine II-H:

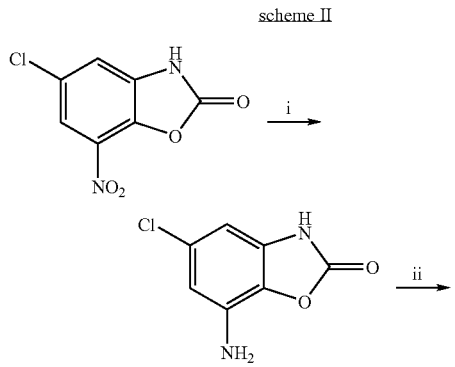

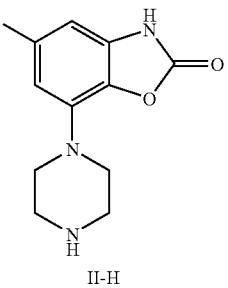

The synthesis of the starting material has been described (patent DE487014).

Scheme II, Step i:

30 g ((0.14 mol) of the starting material was suspended in 600 ml of MeOH. Then a small amount of Raney nickel was added after which hydrogenation was started (atmospheric, room temperature). After 24 hours 7.2 liters (theoretical amount 9.4 liters) of hydrogen was absorbed. To the reaction mixture 150 ml of THF was added and another small amount of Raney nickel. After one hour the reaction mixture was filtered over hyflo, the residue washed with THF. The filtrate was concentrated in vacuo, yielding 25.2 g (98%) of the corresponding aniline.

Scheme II, Step i:

24.2 g (131.2 mmol) of the aniline of the previous step and 25.8 μg (144.3 mmol) of bis (2-chloroethyl)amine were suspended in 675 ml of chlorobenzene. While stirring, 25 ml of solvent were distilled off with the aid of a Dean-Stark apparatus. After removal of the Dean-Stark apparatus, the reaction was allowed to reflux for 48 hours. When the reaction mixture had come to room temperature, the mixture was decanted and the residue washed twice with Et$_2$O. Then 400 ml of MeOH were added after which the mixture was warmed until almost all of the residue was dissolved. Then 200 ml of silica were added after which the whole was concentrated in vacuo. Then the residue was put on top of a flash chromatography column using DMA 0.75 as the eluent. After removal of the solvent a residue was isolated which was suspended in about 100 ml of acetonitrile and stirred for 4 hours. Filtration and drying yielded 17 g of the desired piperazine II-H as a free base.

Synthesis of Amine IV-H:

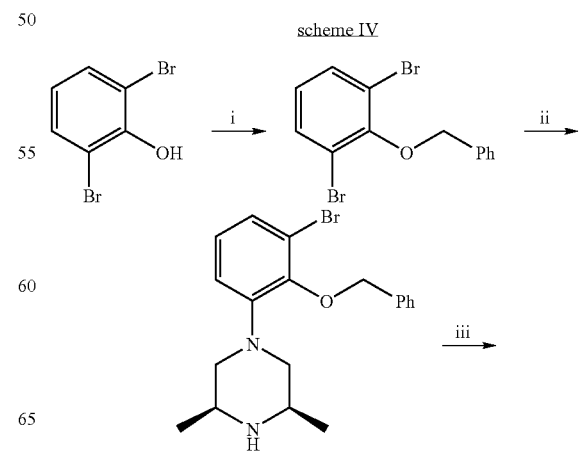

-continued

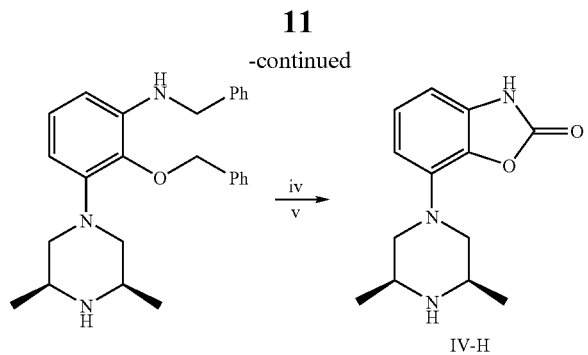

Scheme IV, Step i:

20.5 g (81.3 mmol) of dibromophenol and 20 g of potassium carbonate were suspended in 400 ml of aceton, after which 15.7 ml of benzylbromide were added. The reaction mixture was refluxed for 24 hours. After the mixture had reached room temperature, it was concentrated in vacuo. Subsequently water was added and $CH_2Cl_2$. The organic layer was filtered with a water repellant filter, the dry filtrate concentrated in vacuo after which it was dissolved again in 200 ml of acetonitrile. Subsequently, 15 ml of piperidine were added after which the temperature was raised to 60° C. for one hour. The reaction mixture was concentrated in vacuo and $CH_2Cl_2$ was added. The latter was washed with: 1N HCl (3×), water, 2N NaOH, and again water. The organic layer was filtered with a water repellant filter, the dry filtrate concentrated in vacuo yielding 27.6 g (99%) of the corresponding benzylated phenol.

Scheme IV, Step ii:

The toluene used in this experiment was degassed for three hours prior to usage.

1.48 g (1.61 mmol) of $Pd_2(dba)_3$ and 3.02 g (4.85 mmol) of BINAP were put into 400 ml of toluene after which the mixture was stirred and heated to 105° C. for 0.5 hours after which the mixture was allowed to cool to room temperature. Subsequently were added to the reaction mixture: 27.6 g (80.7 mmol) of the benzylated compound (step i) dissolved in 50 ml of toluene, 9.2 g (80.7 mmol) of the ($\alpha,\alpha'$)-dimethylpiperazine and 10.08 g (104.9 mmol) of sodium tert.butoxide. The resulting mixture was heated at 105° C. for 20 hours, after which it was allowed to reach room temperature. The mixture was diluted with $CH_2Cl_2$ after which it was filtered over hyflo and concentrated in vacuo. The residue was put on top of a flash chromatography column ($SiO_2$) using DMA 0.125. The combined product containing fractions yielded after concentration in vacuo 7.7 g (26%) of the almost pure phenylpiperazine.

Scheme IV, Step iii:

This step was done analogously to the procedure described in the previous step ii (scheme IV). In this case benzylamine was used in the Buchwald reaction. Yield: 88%.

Scheme IV, Step iv:

7 ml (98 mmol) of acetyl chloride was added dropwise to 70 ml of cooled absolute ethanol, stirring was continued for 15 minutes. The latter solution was added to a solution of 11.5 g (28.7 mmol) of the dibenzyl product of step iii in 250 ml of methanol. Subsequently 1.5 g of Pd/C (10%) was added, after which the reaction mixture was hydrogenated for 24 hours. The mixture was filtered over hyflo, the filtrate concentrated in vacuo. The residue containing the amino phenol HCl salt was directly used in step v.

Scheme IV, Step v:

The residue (28.7 mmol) obtained in step iv, 52 ml of DIPEA (298 mmol), and 20.9 g (129 mmol) of CDI were added to 750 ml of THF after which the mixture was refluxed for 20 hours under a nitrogen atmosphere. After cooling to room temperature, the mixture was concentrated in vacuo, to the residue $CH_2Cl_2$ and 5% $NaHCO_3$ were added, the whole being stirred for one hour. Extraction with $CH_2Cl_2$ (3×), the water fraction was concentrated and extracted again ($CH_2Cl_2$, 3×). The combined organic fractions were concentrated in vacuo, the residue contained a considerable amount of imidazol. The whole was solved in 120 ml of acetonitrile after which the solution was allowed to reach room temperature. The precipitate which formed was filtered yielding almost pure piperazine IV.

Synthesis of Amine V-H:

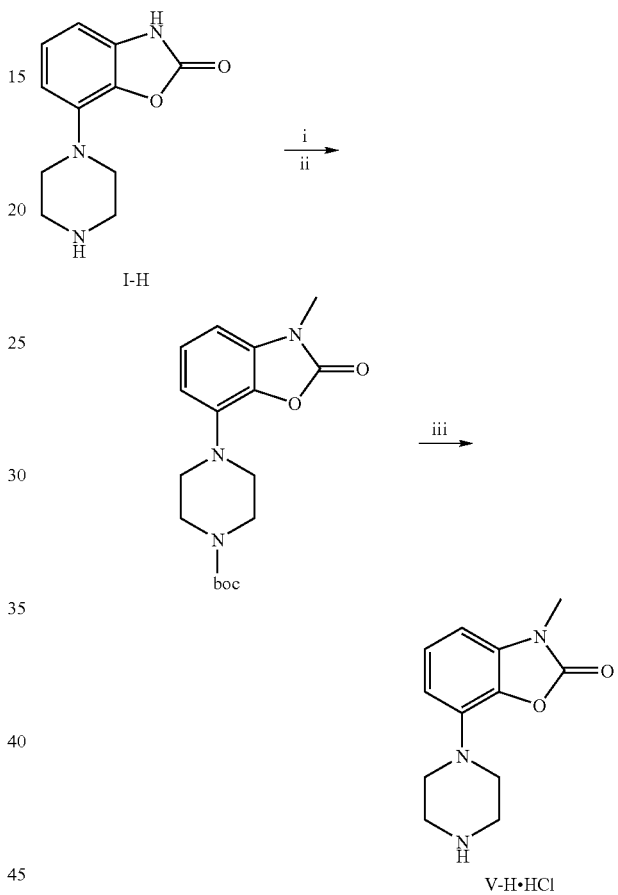

Scheme V, Steps i, ii and iii:

Synthesis of V-H has been described in WO97/36893. The steps i, ii and iii were done analogously to steps i, ii and iii in scheme VI.

Synthesis of Amine VI-H:

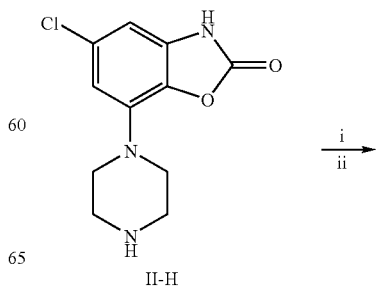

scheme VI

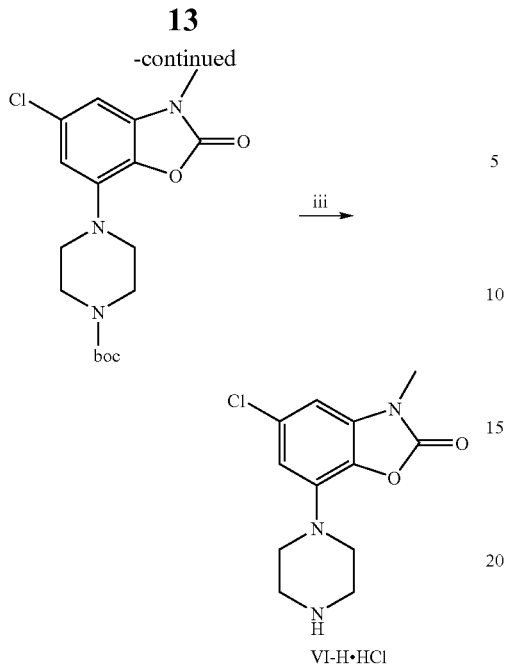

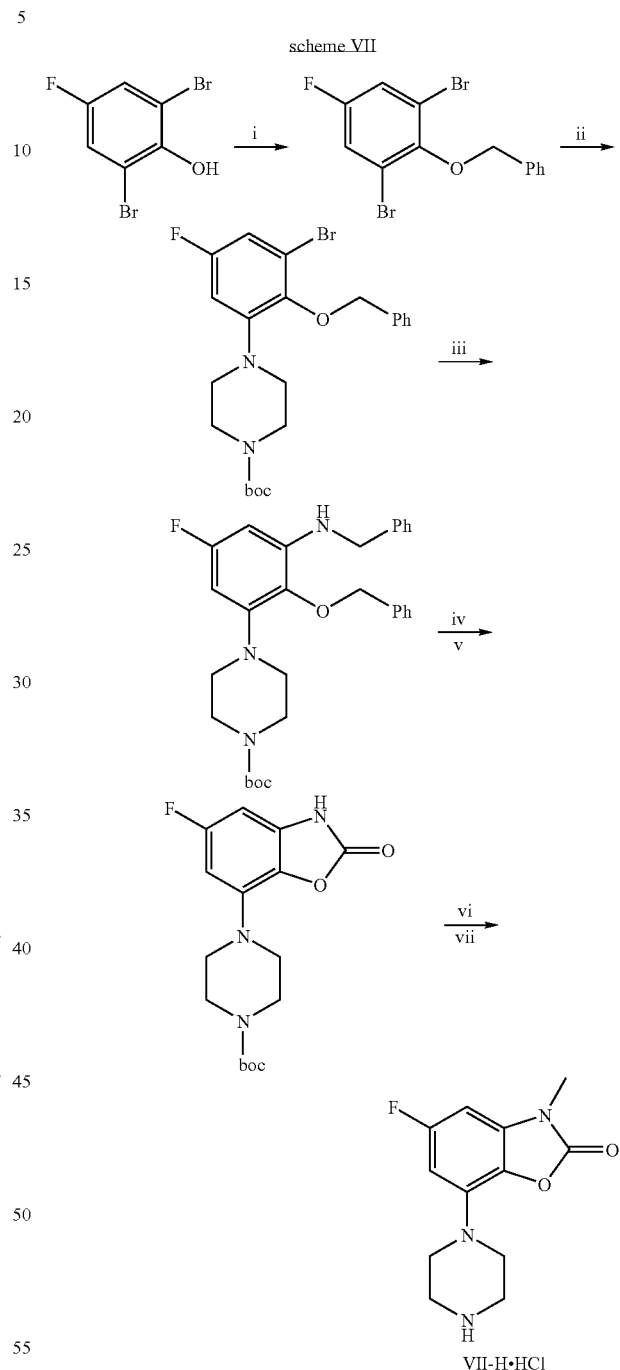

Scheme VI, Step i:

While stirring, 3.8 g (15 mmol) of piperazine II-H were suspended in 5.48 ml (31.5 mmol) of DIPEA and the mixture was brought to −40° C. A solution of 3.14 g (14.4 mmol, 0.96 eq) of Boc-anhydride in 30 ml of $CH_2Cl_2$ was added dropwise in 100 minutes. Stirring was continued at −40° C. (1 hour), then at −30° C. (2 hours), and the reaction mixture was allowed to come to room temperature (16 hours). Then water and some MeOH were added after which it was extracted with $CH_2Cl_2$. The combined organic fractions were filtered with a water repellant filter, the dry filtrate mixed with 50 ml of silica after which the whole was concentrated in vacuo. Then the residue was put on top of a dry chromatography column ($SiO_2$) using $CH_2Cl_2$/MeOH (98/2) as the eluent. The part of the column containing the product was cut out, and the product washed out of the column material with $CH_2Cl_2$/MeOH (98/2) yielding 3.55 g (67%) of the desired N-Boc II.

Scheme VI, Step ii:

4.5 g (12.7 mmol) N-Boc II together with 5.8 g (3.3 eq) of potassium carbonate were suspended in 100 ml of aceton. While stirring, the reaction mixture was cooled to −10° C. after which 0.87 ml (14 mmol, 1.1 eq) of methyl iodide was added dropwise. After 15 minutes, the reaction mixture was allowed to reach room temperature and stirring was continued for 14 hours. Subsequently, the reaction mixture was concentrated in vacuo, the residue mixed with water and $CH_2Cl_2$. The water layer was separated and extracted twice with $CH_2Cl_2$. The combined organic layers were filtered with a water repellant filter, the dry filtrate concentrated in vacuo yielding 4.5 g (98%) of the corresponding N'-methylated N-Boc II.

Scheme VI, Step iii:

While stirring at −10° C., 5 ml of acetyl chloride (70.4 mmol, 5.8 eq) was added dropwise to 65 ml of ethanol. The latter solution was added to 4.5 g (12.2 mmol) of the N'-methylated N-Boc II isolated in step ii. The resulting mixture was stirred for 3 hours at 55° C., then the reaction mixture was allowed to reach room temperature and stirring was continued for 14 hours. Subsequently, the mixture was concentrated in vacuo after which the residue was suspended in di-isopropyl ether and stirred for 2 hours. The precipitate was isolated by filtration yielding 3.6 g (97%) of piperazine VI-H.HCl.

Synthesis of Amine VII-H:

Scheme VII, Step i:

This step was done analogously to step i in scheme IV. After chromatographic purification an oil containing the benzylated product, was isolated in 88% yield. The oil solidified upon standing.

Scheme VII, Step ii:

This step was done analogously to step ii in scheme IV. Boc-piperazine was used in this Buchwald reaction. Yield after chromatographic purification: 44% of a brown oil.

Scheme VII, Step iii:

This step was done analogously to the procedure described in the previous step ii (scheme VII). In this case benzylamine was used in the Buchwald reaction. Yield after chromatographic purification: 73% of a brown oil.

Scheme VII, Step iv:

11.91 g (24.3 mmol) of the debenzylated product isolated in previous step iii (scheme VII) was suspended in a mixture of 110 ml of ethanol, 72 ml of water and 11 ml of acetic acid. While stirring, 0.5 g of Pd(OH)$_2$/C was added and hydrogenation was started for 6 days. After one day and after 3 days an additional small amount of Pd(OH)$_2$/C was added. The reaction mixture was filtered over hyflo, the filtrate concentrated in vacuo. The residue was treated with toluene and concentrated in vacuo, this procedure was repeated, leaving a dark syrup 7.9 g (88%), containing the amino phenol.

Scheme VII, Step v:

This step (ring closure with CDI) was done analogously to step v in scheme IV. The crude product after work up was chromatographed (flash column, SiO$_2$, eluent DCM/MeOH 97/3) yielding 7.6 g of an impure brown foam. A second chromatography (flash column, SiO$_2$, eluent EtOAc/petroleum ether 1/2) yielded 3.3 g (42%) of pure brown foam, containing the N-Boc protected benzoxazolinone piperazine.

Scheme VII, Step vi:

This methylation step was done analogously to the procedure described in step ii (scheme VI). Yield: 98% of a brown foam of 97% purity.

Scheme VII, Step vii:

This deprotection step was done analogously to the procedure described in step iii (scheme VI). Yield: 94% of a light pink solid of 98% purity, containing the product VII-H.HCl.

Synthesis of Amine VIII-H:

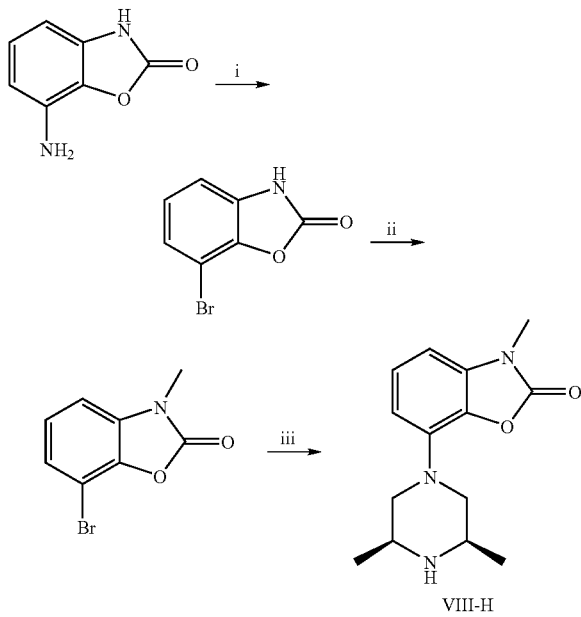

scheme VIII

VIII-H

Scheme VIII, Step i:

The starting material synthesis has been described in EP0189612.

4.91 g (32.7 mmol) of the aniline was suspended in 75 ml of 48% of HBr/water, while it was cooled to −5° C. Subsequently 2.27 g (33 mmol) of sodium nitrite dissolved in 4 ml of water, were added dropwise during 15 minutes. Stirring was continued at 0° C. for 15 minutes.

Subsequently, the reaction mixture was added, in one time, to a 0° C. solution of 2.42 g (16.9 mmol) CuBr in 20 ml of 48% HBr/water. After 30 minutes the reaction mixture was heated to 85° C. for one hour, after which it was allowed to reach room temperature, stirring was continued for 14 hours. To the mixture diethyl ether and water were added, after shaking the organic layer was isolated which was washed with water. The organic layer, together with some silica, was concentrated in vacuo, and the residue was put on top of a flash chromatography column (SiO$_2$) using Et$_2$O/petroleum ether (1/1), and later on pure Et$_2$O as the eluent. The combined product containing fractions yielded after concentration in vacuo 3.3 g (47%) of the desired corresponding bromo product.

Scheme VIII, Step ii:

This step was carried out identical to step ii in scheme VI. Yield: 92% of the corresponding methylated bromo compound.

Scheme VIII, Step iii:

In the following order 6.82 g (29.9 mmol) of the methylated bromo compound, 4.03 g (35.9 mmol) of the dimethyl piperazine, 13.6 g (41.9 mmol) of Cs$_2$CO$_3$, 1.42 g (2.99 mmol) of X-Phos (see Huang et al., *J. Am. Chem. Soc.*, 125 (2003) 6653), and 0.55 g (0.6 mmol) of Pd$_2$(dba)$_3$ were added to 225 ml of toluene which was degassed for 4 hours prior to usage. While stirring and under a nitrogen atmosphere the temperature was raised to 100° C. for 20 hours, after which it was allowed to reach room temperature. The mixture was diluted with CH$_2$Cl$_2$ after which it was filtered and concentrated in vacuo. The residue was put on top of a flash chromatography column (SiO$_2$) using DMA 0.25. The combined product containing fractions yielded after concentration in vacuo 0.73 g (9%) of the desired pure piperazine VIII-H.

Synthesis of Amine IX-H:

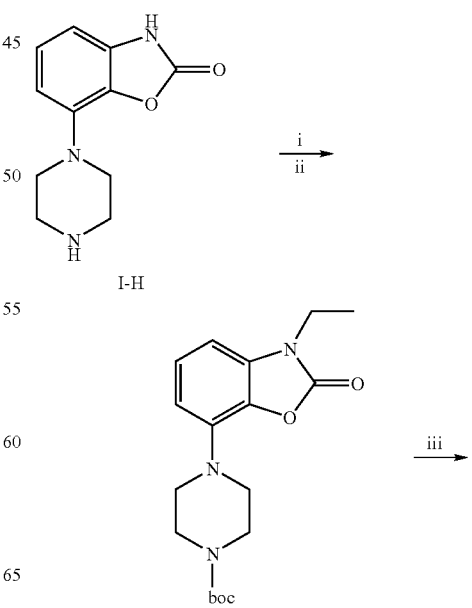

scheme IX

I-H

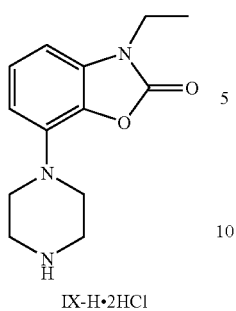
IX-H·2HCl
Scheme IX, Steps i, ii and iii:
Synthesis of I-H has been described in WO97/36893. The steps i, ii and iii were done analogously to steps i, ii and iii in scheme VI.
Below, the various forms Q1-Q26 are given:
1
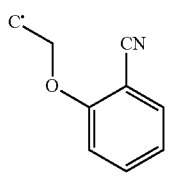
2
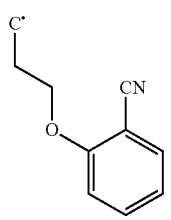
3
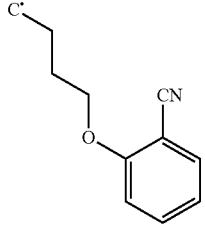
4
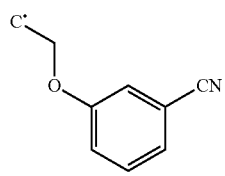
5
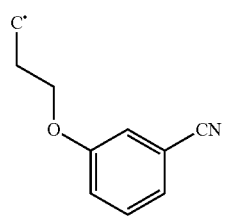
6
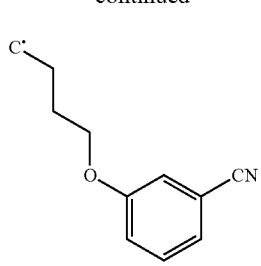
7
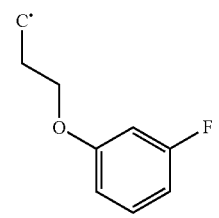
8
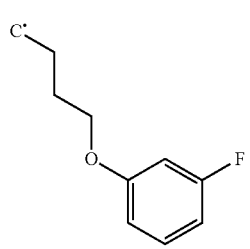
9
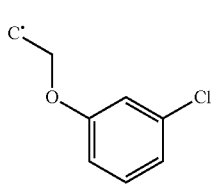
10
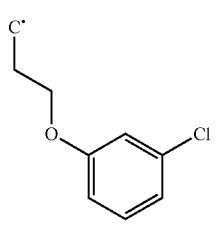
11
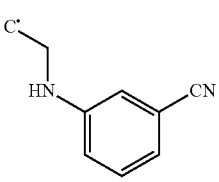
12

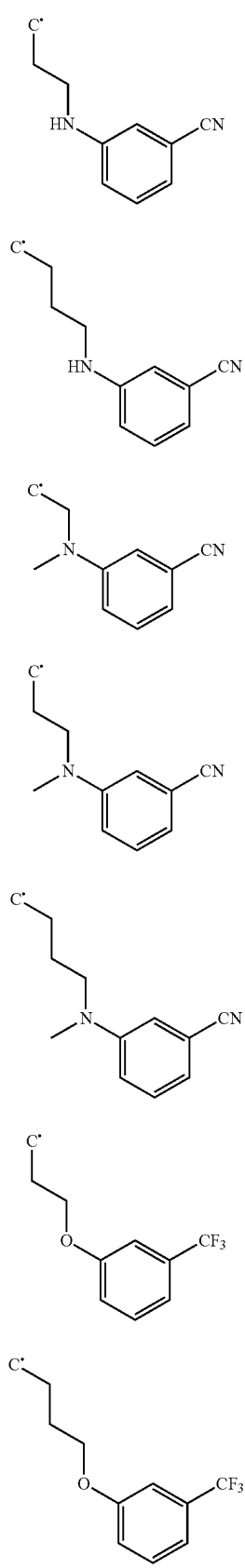
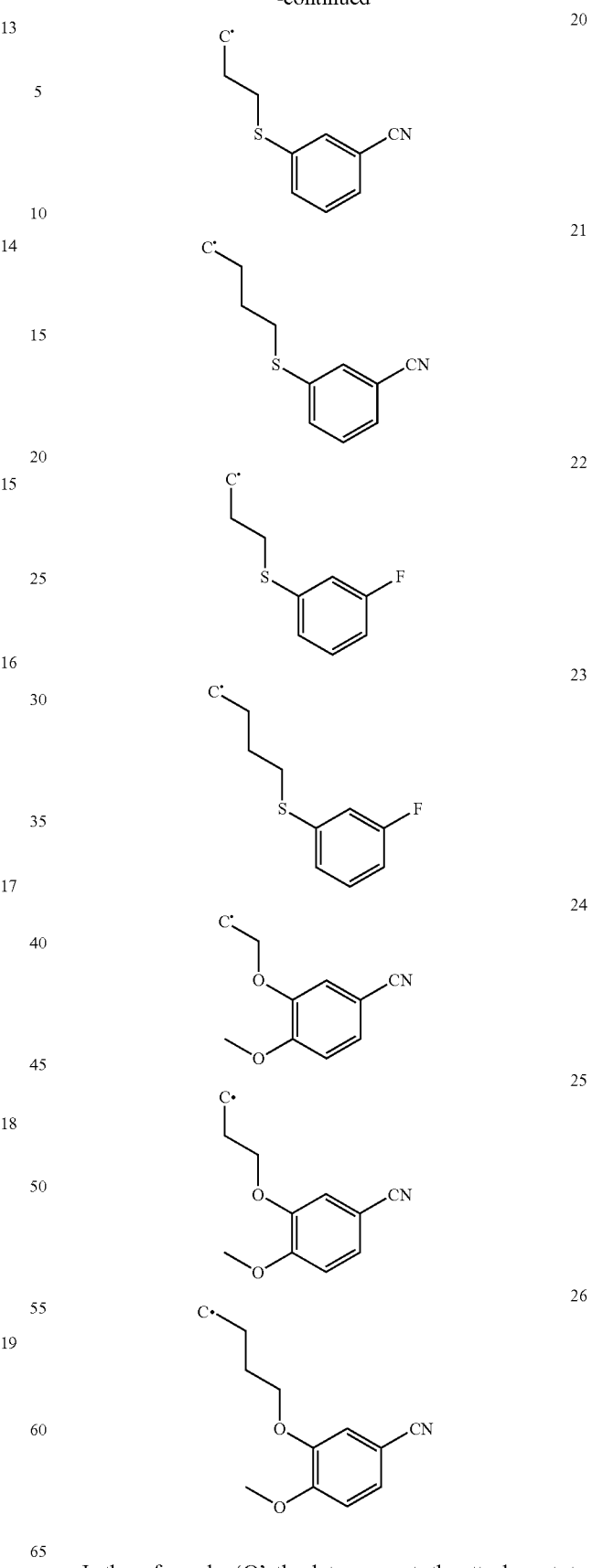
In these formulae 'Q', the dot represents the attachments to the phenylpiperazine part of the compounds of formula (1).

Synthesis of Q1-11, 18-19, 24-26:

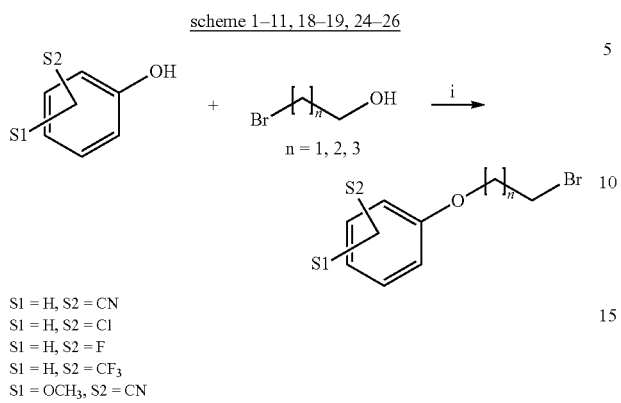

S1 = H, S2 = CN
S1 = H, S2 = Cl
S1 = H, S2 = F
S1 = H, S2 = CF₃
S1 = OCH₃, S2 = CN

All starting phenols (except where S1=2-OCH₃, S2=5-CN, see scheme 1-11, 18-19, 24-26; b) and alcohols were commercially available.

Scheme 1-11, 18-19, 24-26; Step i:

To a stirred solution of 3-fluorophenol (7 ml, 77.43 mmol), PPh₃ (26.4 g, 101 mmol) and 4-bromo-1-butanol (13.35 ml, 123.9 mmol) in 275 ml Toluene at 0° C. under an nitrogen atmosphere, was added dropwise a solution of DIAD (30.46 ml, 155 mmol) in 60 ml toluene (the temperature was kept between 0° C. and 5° C. during the addition). The reaction mixture was stirred for 20 hours at room temperature. The solution was evaporated under reduced pressure and 300 ml of Et₂O/petroleum ether 1:1 was added to the residue. The precipitate which formed during stirring for 30 minutes at room temperature was filtered off and washed 2 times with Et₂O/petroleum ether 1:3 (50 ml). The filtrate was evaporated under reduced pressure and the residue was chromatographed using DCM/petroleum ether 1:4 as eluent to give 18.39 g (96%) of the ether Q9-Br as a colorless oil.

Synthesis of Phenols with S1=2-OCH₃ and S2=5-CN:

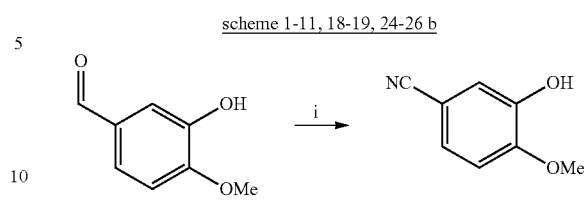

Scheme 1-11, 18-19, 24-26; b, Step i:

A mixture of 3-hydroxy-4-methoxybenzaldehyde (31.4 g, 206.6 mmol) and hydroxyl-amine monohydrochloride (18.7 g, 268.6 mmol) in 165 ml formic acid was refluxed for 1 h. The reaction mixture was cooled to room temperature and 1 liter of ice water was added. The precipitate was filtered and the residue washed with ice water. The solid was further dried by co-evaporation with acetonitrile yielding 13.84 g (45%) of a solid, containing the 2-methoxy-5-cyano-phenol.

Synthesis of Q12-17:

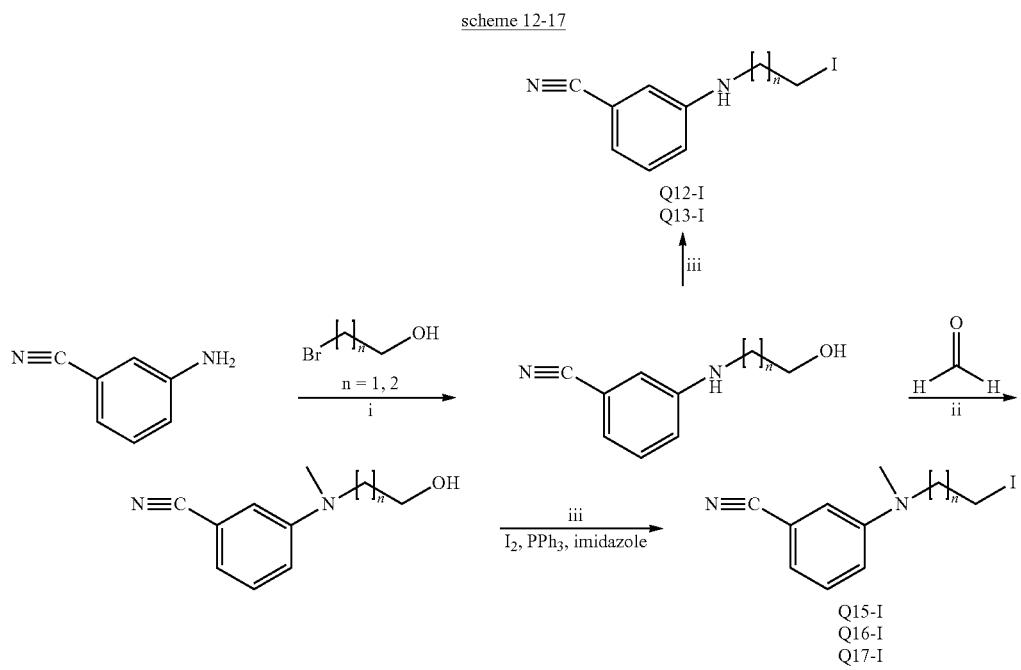

Scheme 12-17 Step i:

For n=2 and 3-cyanoaniline:

A mixture of 3-cyanoaniline (2.95 g, 25 mmol), NaI (7.5 g, 50 mmol), DIPEA (4.3 ml, 25 mmol) and 3-bromo-1-propanol (2.25 ml, 25 mmol) in 50 ml butyronitrile was refluxed for 24 h. The solvent was evaporated under reduced pressure. H₂O and CH₂Cl₂ were added to the residue and after separation the organic layer was dried (Na₂SO₄). The drying agent was removed by filtration and the solvent by evaporation under reduced pressure. The residue was chromatographed (SiO₂) using CH₂Cl₂/CH₃OH/NH₃ 92/7.5/0.5 as the eluent to give 3.45 g (78.4%) of the N-alkylated product Q13-OH as an oil.

Scheme 12-17 Step ii:

To a stirred solution of the N-alkylated product from step i (3.3 g, 18.8 mmol), 37% formaldehyde solution (14 ml, 188 mmol) and NaCNBH$_3$ (3.7 g, 56.4 mmol) in 70 ml CH$_3$CN was added dropwise 1.8 ml glacial acetic acid in 20-minutes. The reaction mixture was stirred for 2 hours at room temperature. Another 1.5 ml glacial acetic acid was added dropwise and stirring was continued for 30 minutes at room temperature. Et$_2$O was added to the reaction mixture and the ether fraction was washed 2 times with 1N NaOH. The combined organic fractions were dried (Na$_2$SO$_4$). The drying agent was removed by filtration and the solvent by evaporation under reduced pressure. The residue was chromatographed (SiO$_2$) using CH$_2$Cl$_2$/CH$_3$OH/NH$_3$ 9217.5/0.5 as the eluent to give 1.80 g (50.4%) of the N-methylated alcohol Q16-OH as a thick oil.

Scheme 12-17 Step iii:

PPh$_3$ (3.1 g, 11.9 mmol) and imidazole (0.83 g, 11.9 mmol) were dissolved in 100 ml CH$_2$Cl$_2$. I$_2$ (3.1 g, 11.9 mmol) was added and the resulting suspension was stirred for 20 minutes at room temperature. A solution of the alcohol Q16-OH (from step ii)(1.8 g, 9.47 mmol) in 8 ml CH$_2$Cl$_2$ was added dropwise and the reaction mixture was stirred for 20 hours at room temperature. H$_2$O was added and after separation the CH$_2$Cl$_2$ fraction was dried (Na$_2$SO$_4$). The drying agent was removed by filtration and the solvent by evaporation under reduced pressure. The residue was chromatographed (SiO$_2$) using CH$_2$Cl$_2$ as eluent to give 2.18 g (76.8%) of the iodide Q16-I as a thick oil.

Q14 needed another approach:

scheme 12-17 b

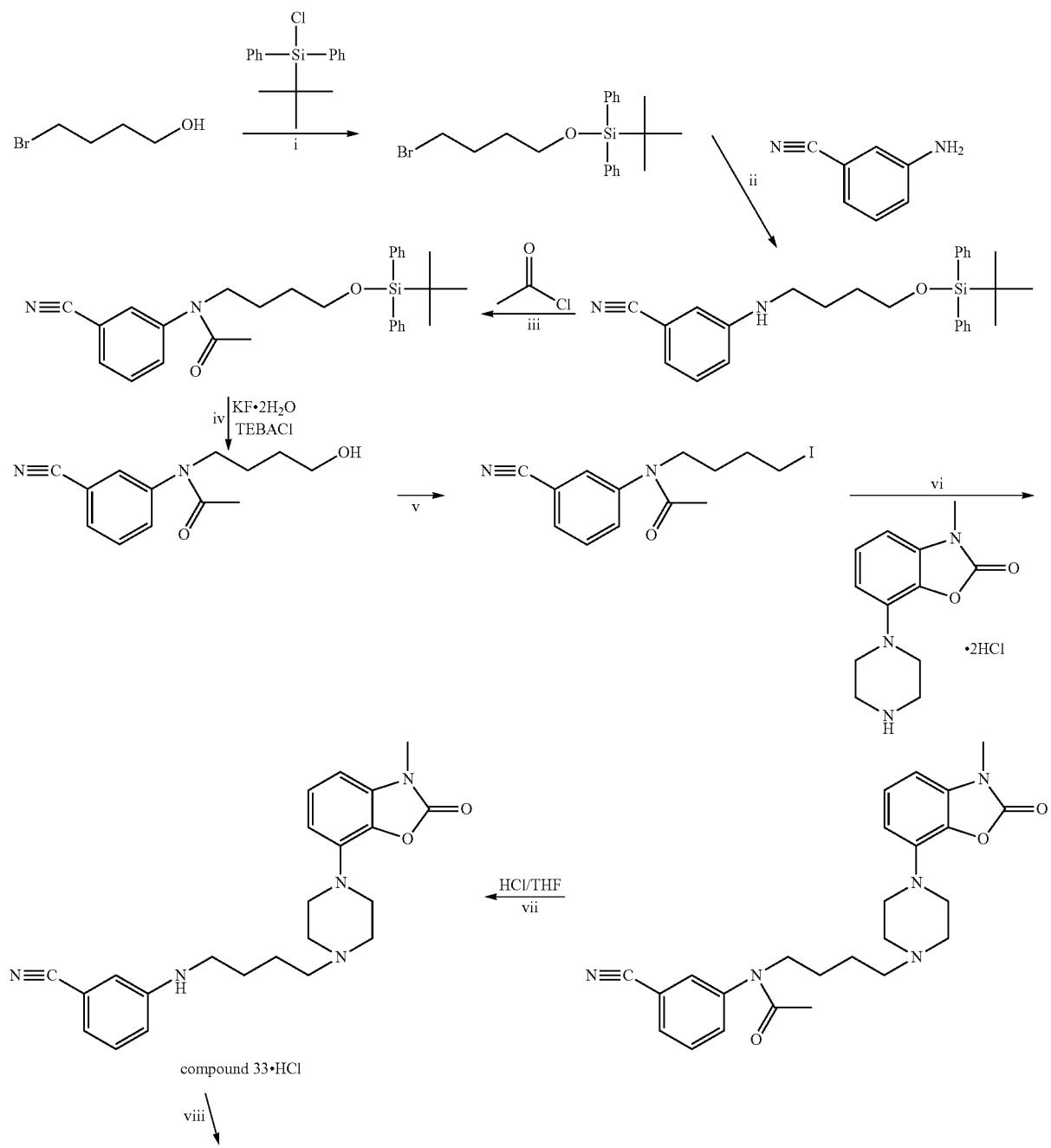

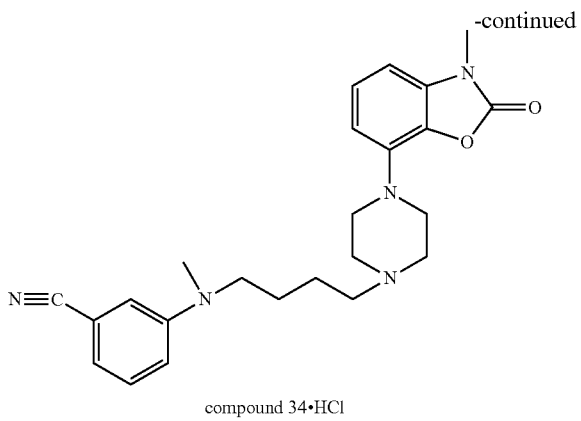

compound 34•HCl

Scheme 12-17 b Step i:

To a stirred solution of 4-bromo-1-butanol (12 g, 78.4 mmol), imidazole (5.86 g, 86.2 mmol) in 70 ml DMF was added tert-butyldiphenylsilylchloride (20.4 ml, 78.4 mmol). The reaction mixture was stirred for 72 hours at room temperature The DMF was removed by evaporation under reduced pressure after which $H_2O$ and $CH_2Cl_2$ were added. The $CH_2Cl_2$ fraction was dried ($Na_2SO_4$). The drying agent was removed by filtration and the solvent by evaporation under reduced pressure. The residue was chromatographed ($SiO_2$) using $CH_2Cl_2$/petroleum ether 1:4 as eluent to give 16.6 g (54.2%) of the silylated alcohol as an oil.

Scheme 12-17 b Step ii:

A mixture of 3-cyanoaniline (4.53 g, 38.36 mmol), silylated alcohol (from step i)(15 g, 38.36 mmol), DIPEA (6.64 ml, 38.36 mmol) and NaI (11.5 g, 76.73 mmol) in 400 ml butyronitrile was refluxed for 24 h. The solvent was evaporated under reduced pressure. $H_2O$ and $CH_2Cl_2$ were added to the residue and after separation the organic layer was dried ($Na_2SO_4$). The drying agent was removed by filtration and the solvent by evaporation under reduced pressure. The residue was chromatographed ($SiO_2$) using $CH_2Cl_2$ as eluent to give 7.17 g (43.7%) of the alkylated aniline as an oil.

Scheme 12-17 b Step iii:

A mixture of the alkylated aniline (from step ii)(1 g, 2.34 mmol), acetyl chloride (0.17 ml, 2.34 mmol), DIPEA (0.40 ml, 2.34 mmol) in 15 ml $CH_2Cl_2$ was stirred at room temperature for 1 h. The solvent was evaporated under reduced pressure and the residue was chromatographed ($SiO_2$) using $CH_2Cl_2$/MeOH 98:2 as the eluent to give 0.88 g (80%) of the acylated aniline as a thick oil.

Scheme 12-17 b Step iv:

A mixture of the acylated aniline (from step iii)(0.88 g, 1.87 mmol), $KF.2H_2O$ (0.26 g, 2.81 mmol), benzyltriethylammoniumchloride (0.37 g, 2.06 mmol) in 21 ml $CH_3CN$ was refluxed for 4 h. The solvent was evaporated under reduced pressure. $H_2O$ and $CH_2Cl_2$ were added to the residue and after separation the organic layer was dried ($Na_2SO_4$). The drying agent was removed by filtration and the solvent by evaporation under reduced pressure. The residue was chromatographed ($SiO_2$) using $CH_2Cl_2$/$CH_3OH$/$NH_3$ 92/7.5/0.5 as the eluent to give 0.31 g (71.4%) of the alcohol as a thick oil.

Scheme 12-17 b Step v:

The conversion of the resulting alcohols to the corresponding iodo derivatives was executed according to the procedure described in scheme 12-17 step iii.

Scheme 12-17 b Step vi:

A mixture of the piperazine (0.41 g, 1.34 mmol), the iodide from step v (0.46 g, 1.34 mmol), DIPEA (0.88 ml, 5.11 mmol) and NaI (0.2 g, 1.34 mmol) in 50 ml $CH_3CN$ was refluxed for 24 h. The solvent was evaporated under reduced pressure. $H_2O$ and $CH_2Cl_2$ were added to the residue and after separation the organic layer was dried ($Na_2SO_4$). The drying agent was removed by filtration and the solvent by evaporation under reduced pressure. The residue was chromatographed ($SiO_2$) using $CH_2Cl_2$/$CH_3OH$/$NH_3$ 96/3.75/0.25 as eluent to give 0.25 g (41.7%) of the alkylated piperazine as a thick oil.

Scheme 12-17 b Step vii:

To a stirred solution of the alkylated piperazine from step vi (0.25 g, 0.56 mmol) in 10 ml THF was added 10 ml 1N HCl. The reaction mixture was reluxed for 6 h. Nothing had happened, so 5 ml of concentrated HCl (36-38%) was added and the reaction mixture was refluxed for 24 h. The THF and $H_2O$ were removed by evaporation under reduced pressure after which a $K_2CO_3$ solution and $CH_2Cl_2$ were added. The $CH_2Cl_2$ was dried ($Na_2SO_4$) and evaporated under reduced pressure. The residue was chromatographed ($SiO_2$) using $CH_2Cl_2$/$CH_3OH$/$NH_3$ 96/3.75/0.25 as eluent. The residual oil was dissolved in ethylacetate and 1 eq. of AcCl/EtOH (1.0 M) was added. The precipitate was filtered to give 0.25 g (100%) of the de-acylated product as a white solid, containing compound 33.HCl, m.p. 174-176° C.

Scheme 12-17 b Step viii:

Compound 34.HCl was made from 33.HCl by a simple methylation according to the procedure described in scheme VI, step ii. Formation of the HCl salt by treatment of 1 equivalent 1M AcCl/MeOH.

Synthesis of Q20-21:

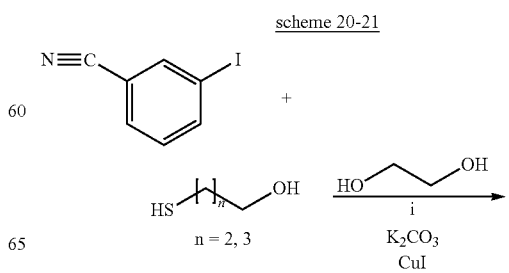

scheme 20-21

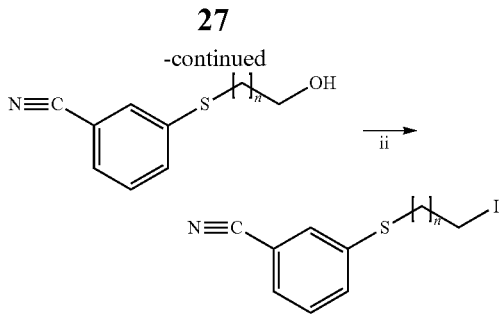

Scheme 20-21 Step i:

The starting iodobenzene and alcohols were commercially available.

A mixture of 3-iodobenzonitrile (2.29 g, 10 mmol), 4-mercapto-1-butanol (1.03 ml, 10 mmol), ethylene glycol (1.12 ml, 20 mmol), $K_2CO_3$ (2.78 g, 20 mmol) and CuI (95 mg, 0.5 mmol) in 40 ml 2-propanol under a nitrogen atmosphere was refluxed for 24 h. The solvent was evaporated under reduced pressure. Aqueous $NH_4OH$ and $CH_2Cl_2$ were added to the residue and after separation the organic layer was dried ($Na_2SO_4$). The drying agent was removed by filtration and the solvent by evaporation under reduced pressure. The residue was chromatographed ($SiO_2$) using $CH_2Cl_2/CH_3OH/NH_3$ 96:3.75:0.25 as the eluent to give 1.40 g (67.6%) of the thioalkylated benzene Q21-OH as an oil.

Scheme 20-21 Step ii:

The conversion of the resulting alcohols to the corresponding iodo derivatives was performed according to the procedure described in scheme 12-17 step iii.

Q20-OH was prepared analogously to Q21-OH.

Synthesis of Q22-23:

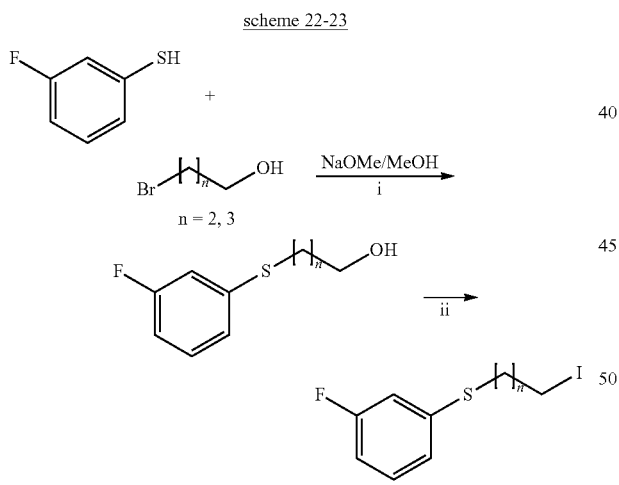

The starting phenol and alcohols were commercially available.

Scheme 22-23 Step i:

To a stirred solution of NaOMe (8.1 g, 150 mmol) in 100 ml methanol under a nitrogen atmosphere, was added dropwise 3-fluorothiophenol (9.5 ml, 100 mmol). The reaction mixture was stirred for 10 minutes at room temperature. 3-bromo-1-propanol (13.6 ml, 150 mmol) was added in one time, after which the reaction mixture was refluxed for 14 hours. After the reaction was allowed to cool, the mixture was concentrated in vacuo after which $H_2O$ and $CH_2Cl_2$ were added to the residue and after separation the organic layer was dried ($Na_2SiO_4$). The drying agent was removed by filtration and the solvent by evaporation under reduced pressure. The residue was chromatographed ($SiO_2$) using $CH_2Cl_2/CH_3OH$ 99/1 as eluent to give 18.5 g (99.5%) of the alkylated product as an oil containing Q22-OH.

Scheme 22-23 Step ii:

The conversion of the resulting alcohols to the corresponding iodo derivatives was executed according to the procedure described in scheme 12-17 step iii.

Q23-OH was prepared analogously to Q22-OH.

The specific compounds of which the synthesis is described above are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only, with a true scope and spirit of the invention being indicated by the claims.

| ABBREVIATIONS | | | | |
|---|---|---|---|---|
| AcCl | acetylchloride | | | |
| ADDP | 1,1'-(azodicarbonyl)dipiperidine | | | |
| CDI | carbonyldiimidazol | | | |
| Dba | see Huang et al., J. Am.Chem.Soc., 125(2003)6653 | | | |
| DCE | dichloroethane | | | |
| DCM | dichloromethane | | | |
| DIAD | diisopropyldiazodicarboxylate | | | |
| DIPE | diisopropylether | | | |
| DIPEA | diisopropylethylamine | | | |
| | $CH_2Cl_2$(ml) | MeOH(ml) | | $NH_4OH$(ml) |
| DMA 0.125 | 980 | 18.75 | | 1.25 |
| DMA 0.187 | 970 | 28.13 | | 1.87 |
| DMA 0.25 | 960 | 37.5 | | 2.5 |
| DMA 0.50 | 920 | 75.0 | | 5.0 |
| DMA 0.75 | 880 | 112.5 | | 7.5 |
| DMA 1.00 | 840 | 150.0 | | 10.0 |
| DMAP | 4-dimethylaminopyridin | | | |
| DME | dimethoxyethane | | | |
| DMF | N,N-dimethylformamide | | | |
| EtOH | ethanol | | | |
| MeOH | methanol | | | |
| MTBE | methyl(tert.)-butylether | | | |
| NMP | N-methylpyrrolidon | | | |
| PA | petroleum ether | | | |
| TBAB | tetrabutylammoniumbromide | | | |
| TBAC | tetrabutylammoniumchloride | | | |
| TBAF | tetrabutylammoniumfluoride | | | |
| THF | tetrahydrofurane | | | |
| XPHOS | see Huang et al., J. Am.Chem.Soc., 125(2003)6653 | | | |

Example

Formulation of Compound 14 Used in Animal Studies

For oral (p.o.) administration: to the desired quantity (0.5-5 mg) of the solid compound 14 in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: to the desired quantity (0.5-15 mg) of the solid compound 14 in a glass tube, some glass beads were added and the solid was milled by vortexing for 2 minutes. After addition of 1 ml of a solution of 1% methyl-cellulose and 5% mannitol in water, the compound was suspended by vortexing for 10 minutes. Finally the pH was adjusted to 7.

Example

Pharmacological Test Results

TABLE 2

In vitro affinities and functional activity of compounds of the invention

| compound | Dopamine-$D_2$ binding p$K_i$ | 5-HT reuptake binding p$K_i$ | Dopamine-$D_2$ cAMP accum $\epsilon$ (intrinsic activity) |
|---|---|---|---|
| 6 | 9.0 | 8.4 | 0.76 |
| 9 | 8.2 | 7.0 | 0.64 |
| 14 | 7.8 | 9.0 | 0.57 |
| 15 | 8.2 | 9.1 | 0.61 |
| 17 | 7.6 | 7.3 | 0.51 |
| 20 | 8.4 | 8.5 | 0.98 |
| 24 | 8.9 | 7.9 | 0.86 |
| 26 | 8.0 | 8.0 | 0.79 |
| 31 | 7.2 | 8.3 | 0.56 |
| 35 | 7.0 | 9.2 | 0.55 |
| Examples from Table A on page 14 of EP 0 900 792 A1 | | | |
| A1 | 8.9 | 6.1 | — |
| A6 | 8.3 | <6.3 | — |
| A12 | 7.9 | <6.3 | — |
| A17 | 7.6 | 6.3 | — |
| A18 | 9.2 | 5.9 | — |
| A22 | 8.3 | <6.3 | — |

Dopamine-$D_2$ and serotonin reuptake receptor affinity data obtained according to the protocols given above are shown in the table below. In vitro functional activity at cloned human dopamine $D_{2,L}$ receptors as measured by accumulation of radiolabeled cAMP (intrinsic activity $\epsilon$). In the lower part of the table, for comparison in vitro receptor binding data are given of benzoxazolone derivatives bearing a terminal phenyl group as disclosed in EP 0 900 792 It concerns the examples A1, A6, A12, A17, A18 and A22 as given in Table A on p. 14 of EP 0 900 792 A1. From the results it is clear that these compounds have a high affinity for dopamine-$D_2$ receptors, but are essentially devoid of serotonin reuptake inhibition.

The invention claimed is:

1. A compound of formula (1),

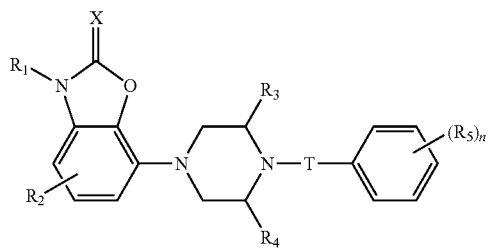

(1)

or a tautomer, a stereoisomer, or an N-oxide thereof, or a salt or hydrate of any of the foregoing, wherein:

X is chosen from a sulphur atom and an oxygen atom;
$R_1$ is chosen from a hydrogen atom, and ($C_1$-$C_6$)alkyl, $CF_3$, $CH_2CF_3$, OH and O—($C_1$-$C_6$)alkyl groups;
$R_2$ is chosen from a hydrogen atom, a halogen, a cyano and a ($C_1$-$C_6$)alkyl group;
$R_3$ is chosen from a hydrogen atom and a ($C_1$-$C_6$)alkyl group;
$R_4$ is chosen from a hydrogen atom and a ($C_1$-$C_6$)alkyl group, wherein said ($C_1$-$C_6$)alkyl group is optionally substituted with a halogen atom;

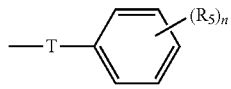

is chosen from:

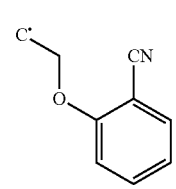

1

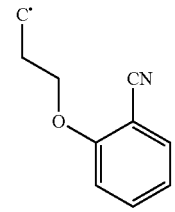

2

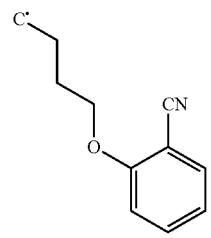

3

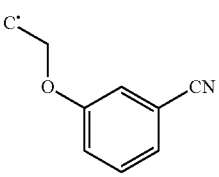

4

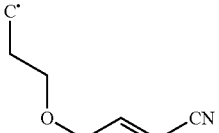

5

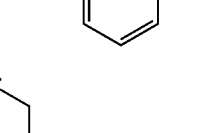

6

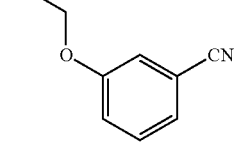

-continued
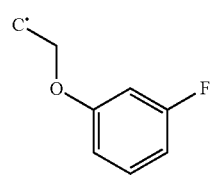
7
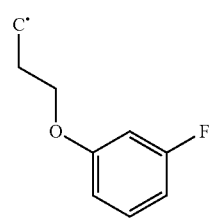
8
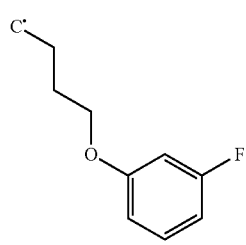
9
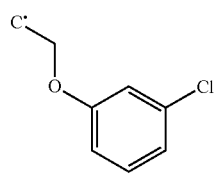
10
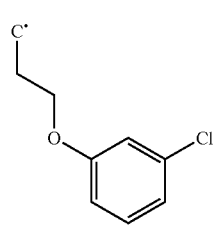
11
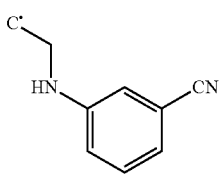
12
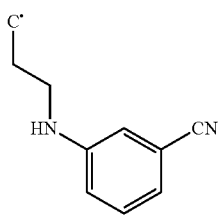
13
-continued
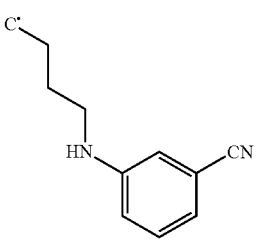
14
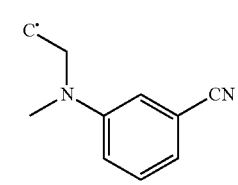
15
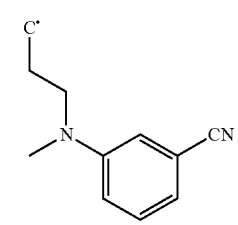
16
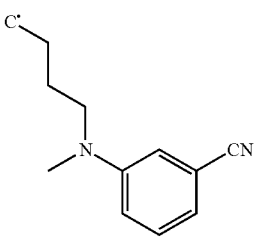
17
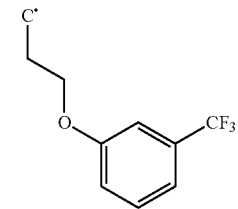
18
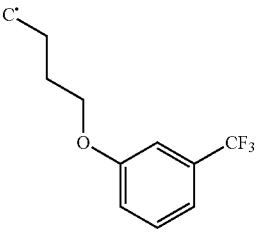
19
20

-continued
21
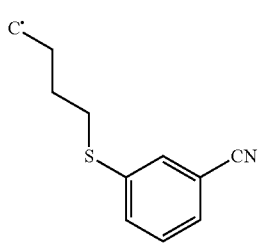
22
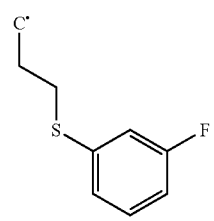
23
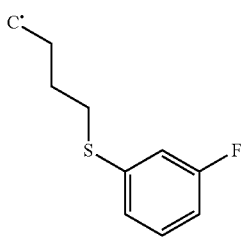
24
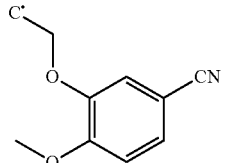
25
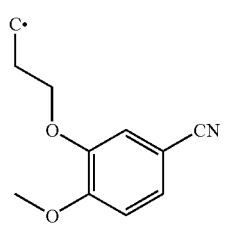
26
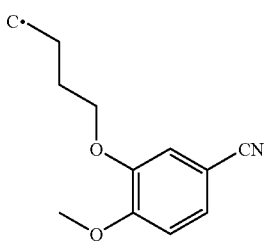
wherein the dot represents the point of attachment to the remaining portion of the compound of formula (1),
wherein the compound of formula (1) exhibits serotonin reuptake inhibition and partial dopamine-$D_2$ receptor agonism, and wherein:
the phenylpiperazine portion of formula (1) is chosen from:
I
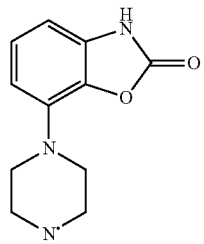
II
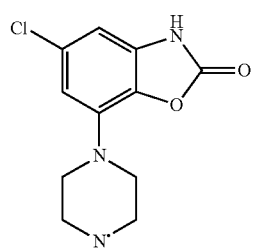
III
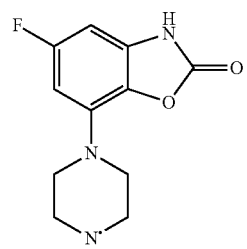
IV
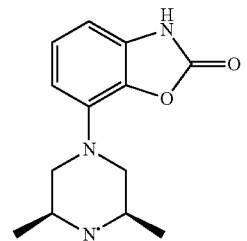
V
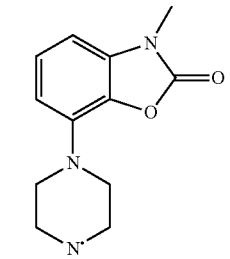
VI
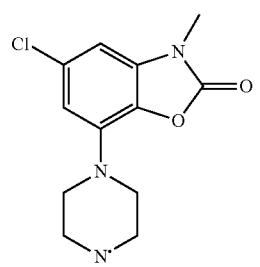

VII

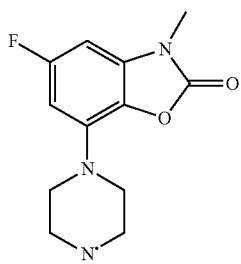

VIII

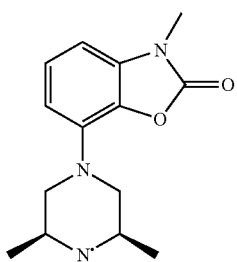

IX

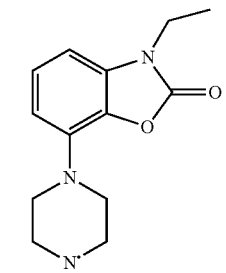

wherein the dot represents the point of attachment of said phenylpiperazine portion of formula (1) to

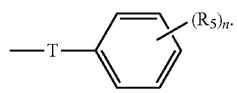

2. A pharmaceutical composition comprising:
at least one pharmaceutically acceptable ingredient chosen from carriers, auxiliary substances, and combinations thereof; and
a pharmacologically active amount of at least one compound of formula (1), (1)

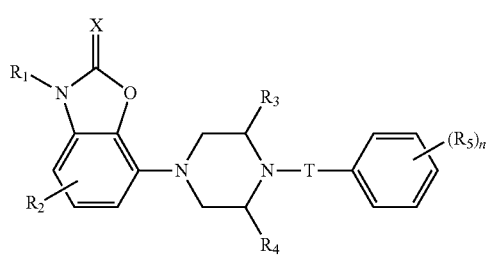

or a tautomer, a stereoisomer, or an N-oxide thereof, or a salt or hydrate of any of the foregoing, or a mixture of any two or more of the foregoing, wherein:
X is chosen from a sulphur atom and an oxygen atom;
$R_1$ is chosen from a hydrogen atom, and $(C_1-C_6)$alkyl, $CF_3$, $CH_2CF_3$, OH and O—$(C_1-C_6)$alkyl groups;
$R_2$ is chosen from a hydrogen atom, a halogen, a cyano and a $(C_1-C_6)$alkyl group;
$R_3$ is chosen from a hydrogen atom and a $(C_1-C_6)$alkyl group;
$R_4$ is chosen from a hydrogen atom and a $(C_1-C_6)$alkyl group, wherein said $(C_1-C_6)$alkyl group is optionally substituted with a halogen atom;

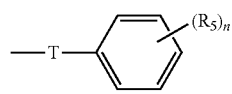

is chosen from:

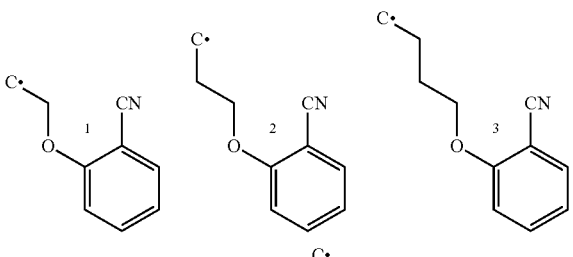

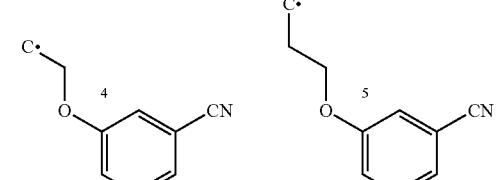

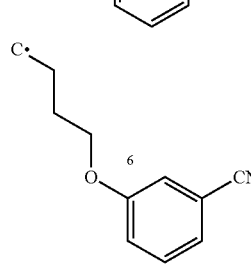

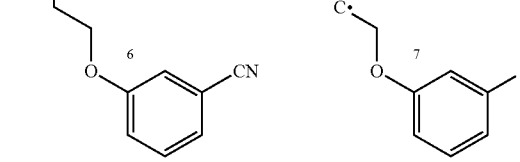

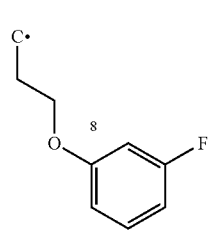

wherein the dot represents the point of attachment to the remaining portion of the compound of formula (1), wherein the compound of formula (1) exhibits serotonin reuptake inhibition and partial dopamine-D$_2$ receptor agonism, and wherein:

the phenylpiperazine portion of the compound of formula (1) chosen from:

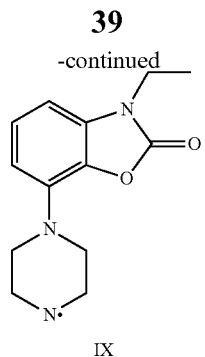

IX wherein the dot represents the point of attachment of said phenylpiperazine portion of formula (1) to

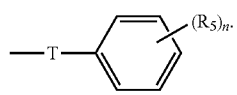

3. A method for preparing a pharmaceutical composition, comprising:
   combining at least one compound of formula (1),

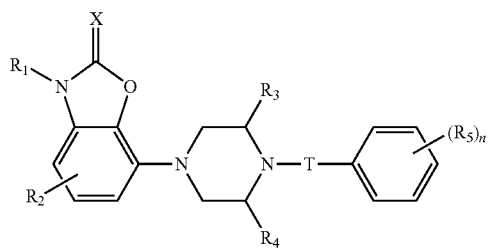
(1)

or a tautomer, a stereoisomer, or an N-oxide thereof, or a salt or hydrate of any of the foregoing, or a mixture of any two or more of the foregoing, wherein:

X is chosen from a sulphur atom and an oxygen atom;

$R_1$ is chosen from a hydrogen atom, and $(C_1\text{-}C_6)$alkyl, $CF_3$, $CH_2CF_3$, OH and $O\text{—}(C_1\text{-}C_6)$alkyl groups;

$R_2$ is chosen from a hydrogen atom, a halogen, a cyano and a $(C_1\text{-}C_6)$alkyl group;

$R_3$ is chosen from a hydrogen atom and a $(C_1\text{-}C_6)$alkyl group;

$R_4$ is chosen from a hydrogen atom and a $(C_1\text{-}C_6)$alkyl group, wherein said $(C_1\text{-}C_6)$alkyl group is optionally substituted with a halogen atom;

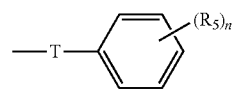

is chosen from:

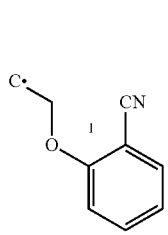
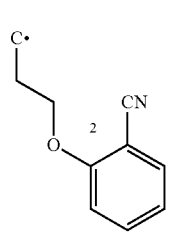
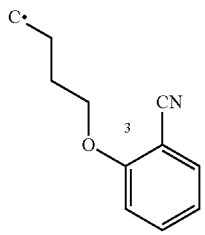

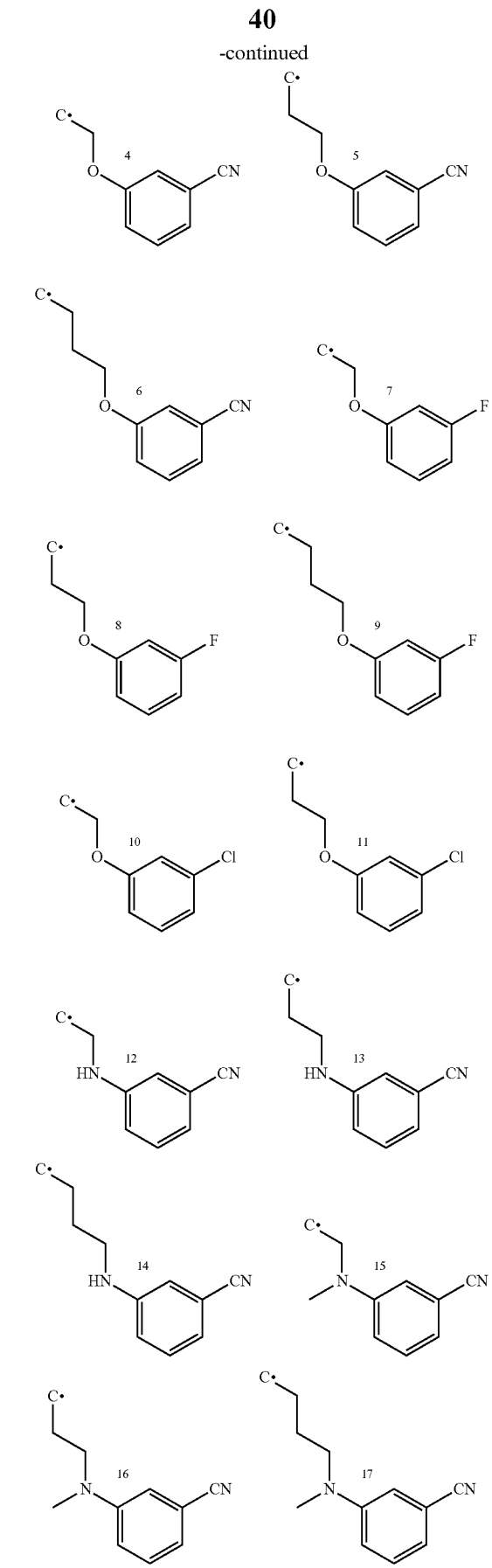

-continued

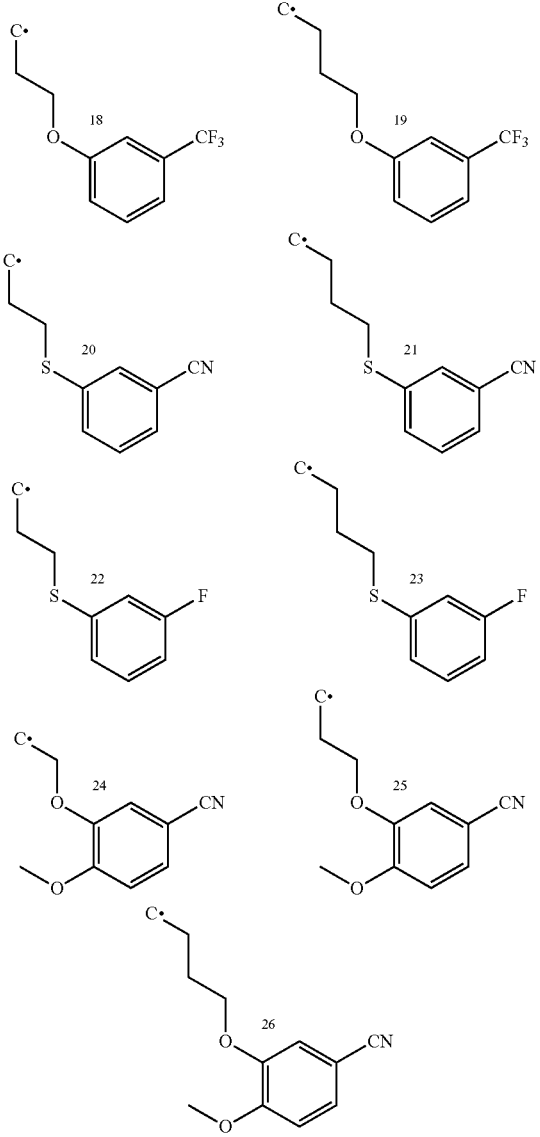

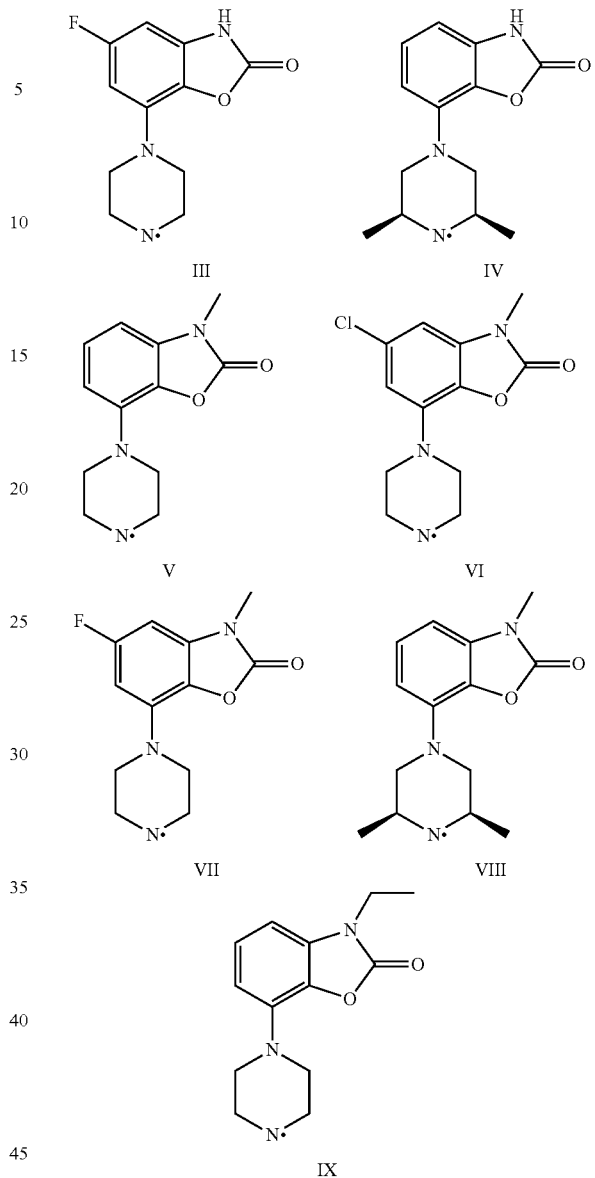

wherein the dot represents the point of attachment to the remaining portion of the compound of formula (1), wherein the compound of formula (1) exhibits serotonin reuptake inhibition and partial dopamine-$D_2$ receptor agonism, and wherein:

the phenylpiperazine portion of formula (1) is chosen from:

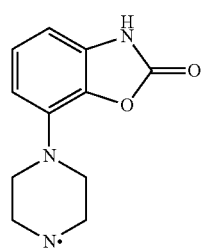 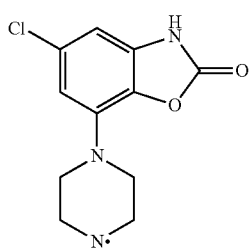

wherein the dot represents the point of attachment of said remaining portion of formula (1) to

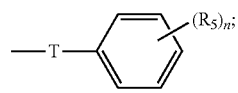

and at least one pharmaceutically acceptable ingredient chosen from carriers, auxiliary substances, and combinations thereof;

wherein said at least one compound of formula (1) is present in an amount effective for treating at least one CNS disorder in a patient in need of treatment thereof.

4. A method for preparing a medicament, comprising:

combining at least one compound of formula (1),

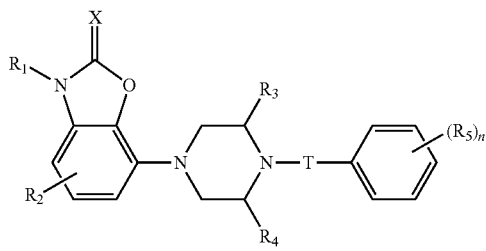

(1)

or at least one tautomer thereof, stereoisomer thereof, or N-oxide thereof, or at least one salt or at least one hydrate of any of the foregoing or a mixture of any two or more of the foregoing, wherein:

X is chosen from a sulphur atom and an oxygen atom;

$R_1$ is chosen from a hydrogen atom, and $(C_1-C_6)$alkyl, $CF_3$, $CH_2CF_3$, OH and O—$(C_1-C_6)$alkyl groups;

$R_2$ is chosen from a hydrogen atom, a halogen, a cyano and a $(C_1-C_6)$alkyl group;

$R_3$ is chosen from a hydrogen atom and a $(C_1-C_6)$alkyl group;

$R_4$ is chosen from a hydrogen atom and a $(C_1-C_6)$alkyl group, wherein said $(C_1-C_6)$alkyl group is optionally substituted with a halogen atom;

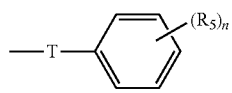

is chosen from:

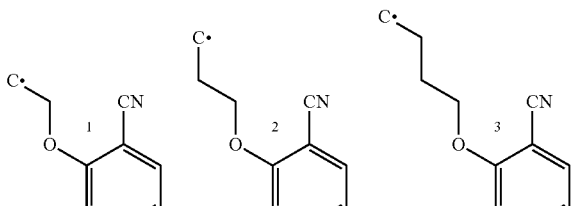

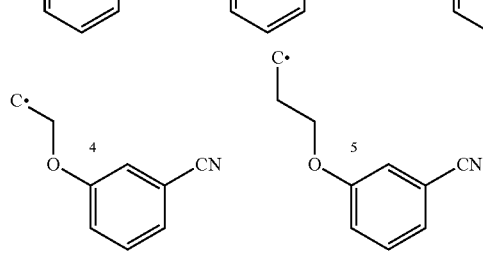

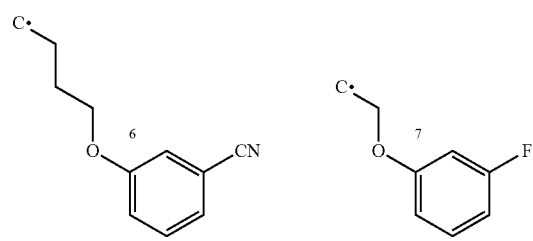

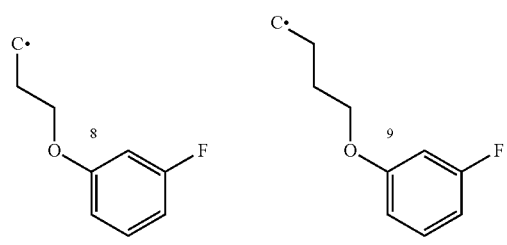

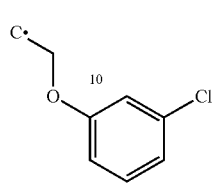

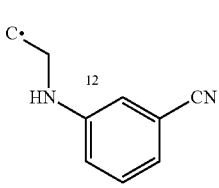

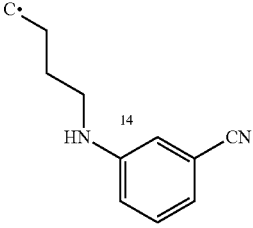

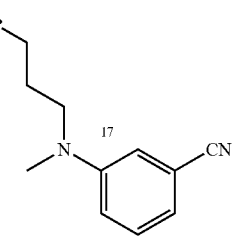

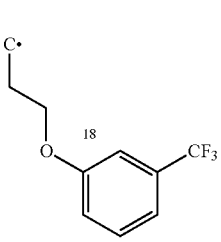

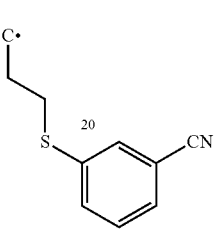

-continued

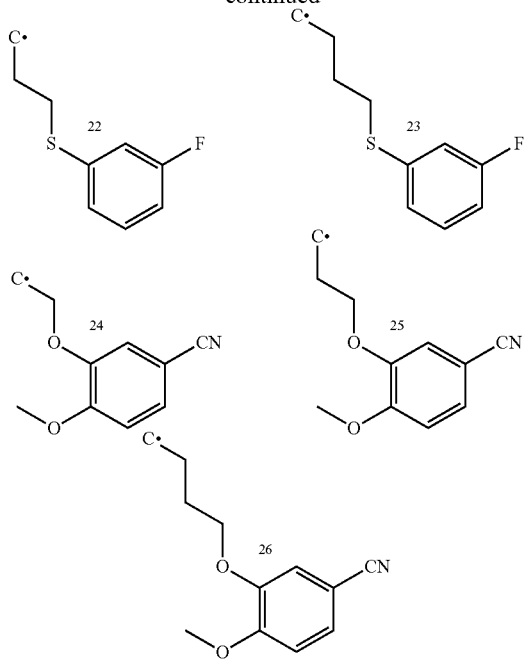

wherein the dot represents the point of attachment to the remaining portion of the compound of formula (1), wherein the compound of formula (1) exhibits serotonin reuptake inhibition and partial dopamine-D$_2$ receptor agonism, and wherein:

the phenylpiperazine portion of formula (1) is chosen from the groups:

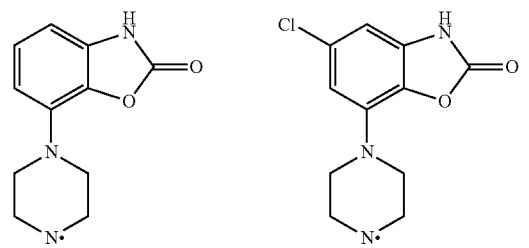
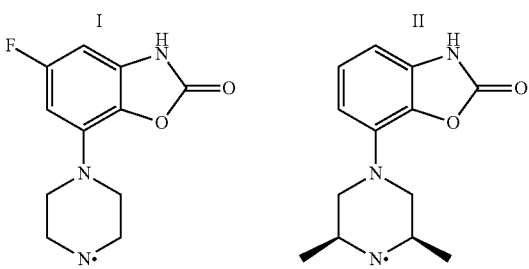
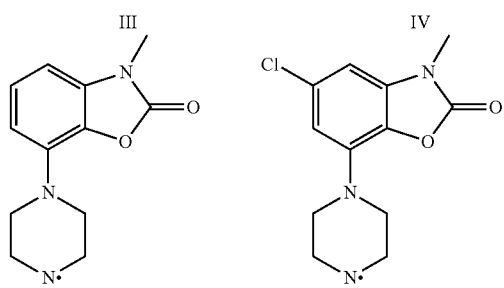

-continued

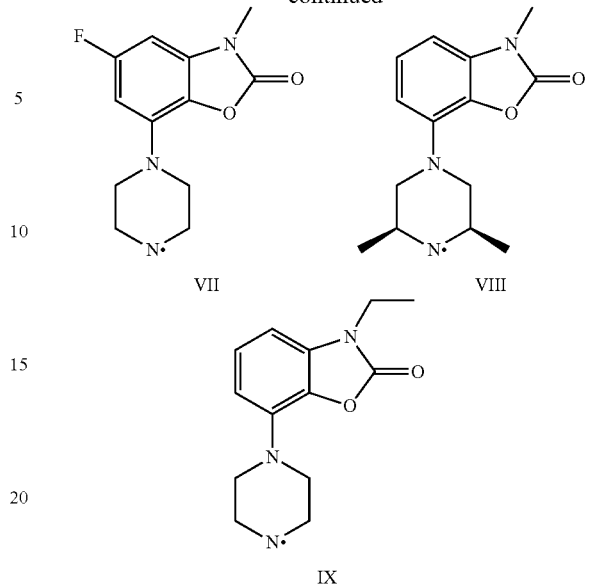

wherein the dot represents the point of attachment of said remaining portion of formula (1) to

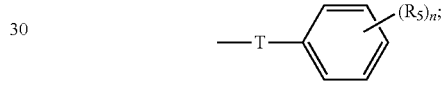

and
at least one pharmaceutically acceptable ingredient chosen from carriers, auxiliary substances, and combinations thereof;
wherein said at least one compound of formula (1) is present in an amount effective for treating at least one CNS disorder in a patient in need of treatment thereof.

5. A method for treating at least one CNS disorder in a patient in need thereof, comprising:
administering a pharmacologically active amount of at least one compound of formula (1),

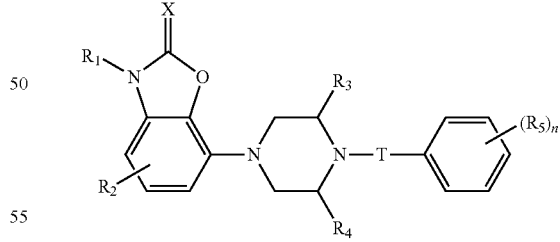

(1)

or a tautomer, a stereoisomer, or an N-oxide thereof, or a salt or hydrate of any of the foregoing, or a mixture of any two or more of the foregoing, wherein:
X is chosen from a sulphur atom and an oxygen atom;
$R_1$ is chosen from a hydrogen atom, and ($C_1$-$C_6$)alkyl, $CF_3$, $CH_2CF_3$, OH and O—($C_1$-$C_6$)alkyl groups;
$R_2$ is chosen from a hydrogen atom, a halogen, a cyano and a ($C_1$-$C_6$)alkyl group;
$R_3$ is chosen from a hydrogen atom and a ($C_1$-$C_6$)alkyl group;

$R_4$ is chosen from a hydrogen atom and a $(C_1-C_6)$alkyl group, wherein said $(C_1-C_6)$alkyl group is optionally substituted with a halogen atom; and
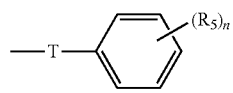
is chosen from:
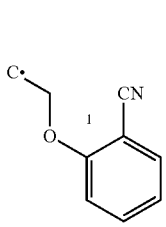
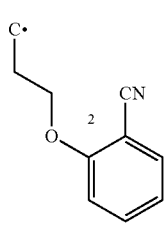
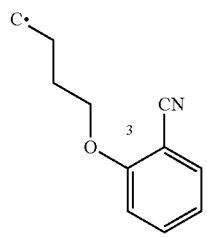
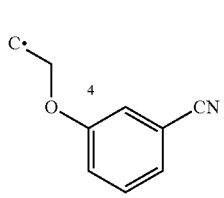
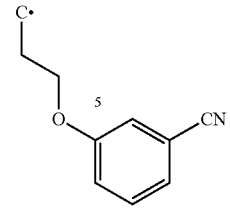
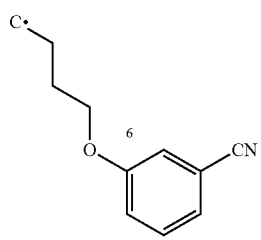
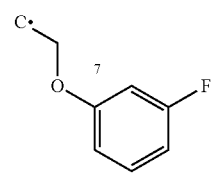
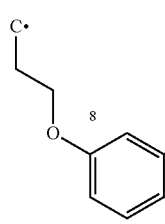
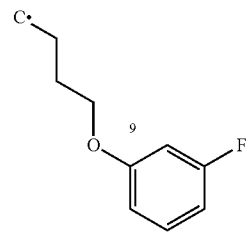
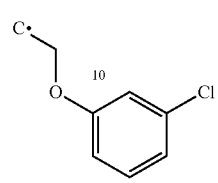
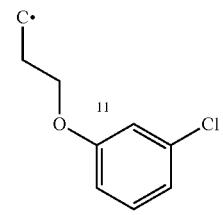
-continued
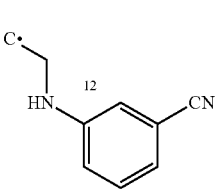
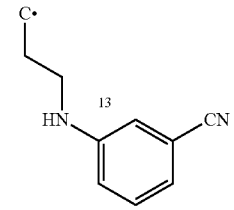
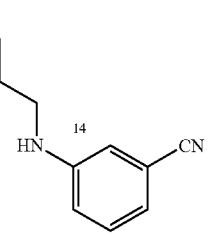
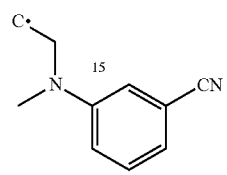
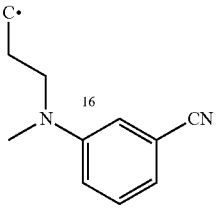
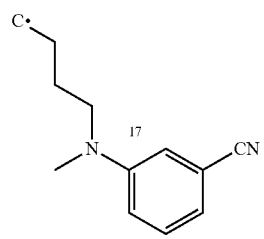
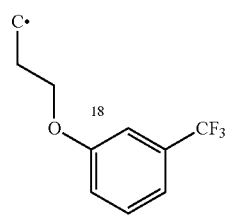
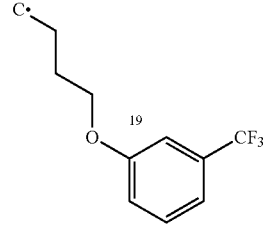
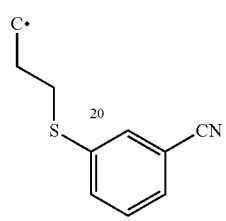
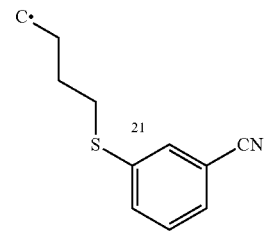
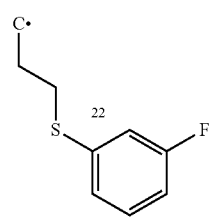
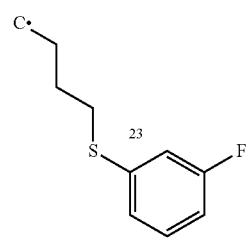

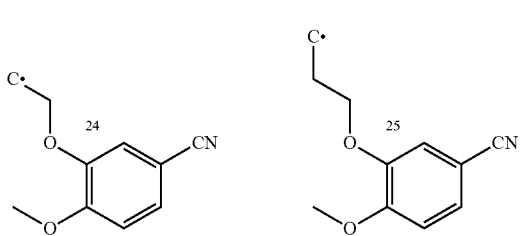
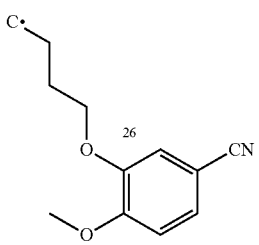

wherein the dot represents the point of attachment to the remaining portion of the compound of formula (1), wherein the compound of formula (1) exhibits serotonin reuptake inhibition and partial dopamine-D$_2$ receptor agonism, and wherein:

the phenylpiperazine portion of formula (1) is chosen from:

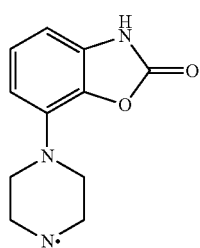
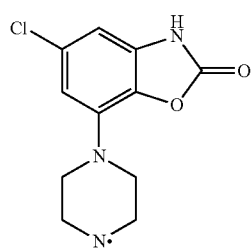
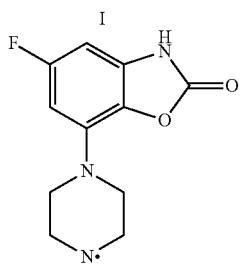
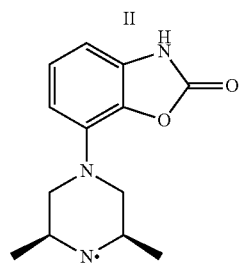

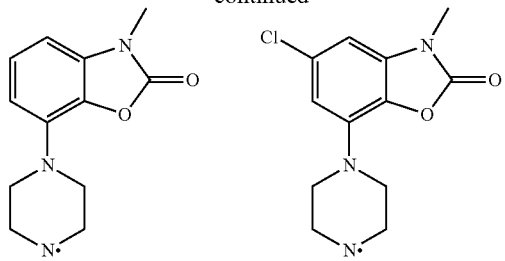
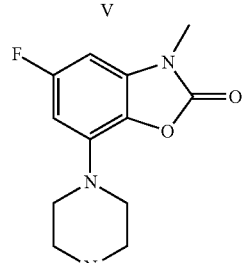
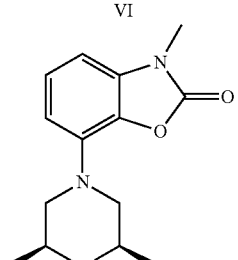
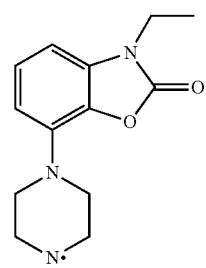

wherein the dot represents the point of attachment of said remaining portion of formula (1) to

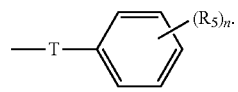

and the at least one CNS disorder is chosen from anxiety disorders, depression, Parkinson's disease, and schizophrenia.

6. The method of claim 5, wherein said at least one CNS disorder is depression.

7. The method of claim 5, wherein said at least one CNS disorder is schizophrenia.

8. The method of claim 5, wherein said at least one CNS disorder is Parkinson's disease.

* * * * *